US012622911B2

(12) United States Patent
Madala

(10) Patent No.: US 12,622,911 B2
(45) Date of Patent: May 12, 2026

(54) METHODS AND COMPOSITIONS FOR THE TREATMENT OF PULMONARY FIBROSIS USING VOLASERTIB

(71) Applicant: Children's Hospital Medical Center, Cincinnati, OH (US)

(72) Inventor: Satish Kumar Madala, Cincinnati, OH (US)

(73) Assignee: CHILDREN'S HOSPITAL MEDICAL CENTER, Cincinnati, OH (US)

( * ) Notice: Subject to any disclaimer, the term of this patent is extended or adjusted under 35 U.S.C. 154(b) by 0 days.

(21) Appl. No.: 17/972,963

(22) Filed: Oct. 25, 2022

(65) Prior Publication Data

US 2023/0127861 A1 Apr. 27, 2023

Related U.S. Application Data

(60) Provisional application No. 63/272,256, filed on Oct. 27, 2021.

(51) Int. Cl.

| | |
|---|---|
| ***A61K 31/519*** | (2006.01) |
| ***A61K 31/4418*** | (2006.01) |
| ***A61K 31/496*** | (2006.01) |
| ***A61K 39/395*** | (2006.01) |
| ***A61P 11/00*** | (2006.01) |

(52) U.S. Cl.

CPC ........ *A61K 31/519* (2013.01); *A61K 31/4418* (2013.01); *A61K 31/496* (2013.01); *A61K 39/3955* (2013.01); *A61P 11/00* (2018.01)

(58) Field of Classification Search

CPC .. C07D 471/04; C07D 487/04; C07D 417/14; C07D 403/14; C07D 405/14; C07D 413/14; C07D 401/12; C07D 401/14; C07D 519/00; A61P 11/00; A61P 7/00; A61K 31/519; A61K 31/4745; A61K 31/675; A61K 31/5377

See application file for complete search history.

(56) References Cited

U.S. PATENT DOCUMENTS

| | | | |
|---|---|---|---|
| 10,973,882 | B2 | 4/2021 | Liang et al. |
| 2008/0038189 | A1 | 2/2008 | Addepalli et al. |
| 2010/0004232 | A1 | 1/2010 | Berdini et al. |
| 2011/0318393 | A1 | 12/2011 | Ladouceur et al. |
| 2013/0289014 | A1 | 10/2013 | Solca et al. |
| 2014/0371233 | A1 | 12/2014 | Strittmatter |
| 2015/0045395 | A1 | 2/2015 | Lee et al. |
| 2015/0328187 | A1 | 11/2015 | Schafer et al. |
| 2021/0213037 | A1 | 7/2021 | Madala et al. |

FOREIGN PATENT DOCUMENTS

| | | | |
|---|---|---|---|
| CN | 104906120 | A | 9/2015 |
| WO | 2004/058781 | A1 | 7/2004 |
| WO | 2006/036883 | A2 | 4/2006 |
| WO | 2009/073224 | A1 | 6/2009 |
| WO | 2010/009985 | A2 | 1/2010 |
| WO | 2010/056931 | A1 | 5/2010 |
| WO | 2012/021974 | A1 | 2/2012 |
| WO | 2012/034942 | A1 | 3/2012 |
| WO | 2015/069217 | A1 | 5/2015 |
| WO | 2016/103223 | A1 | 6/2016 |
| WO | 2018/086584 | A1 | 5/2018 |

OTHER PUBLICATIONS

Yu J, et.al. PLK1 Inhibition alleviates transplant-associated obliterative bronchiolitis by suppressing myofibroblast differentiation. Aging (Albany NY). Jun. 15, 2020;12(12):11636-11652. (Year: 2020).*

Hu M. et. al. Therapeutic targeting of SRC kinase in myofibroblast differentiation and pulmonary fibrosis. J Pharmacol Exp Ther. Oct. 2014;351(1):87-95. (Year: 2014).*

Karimi-Shah, B., and Chowdhury, B. A. Forced Vital Capacity in Idiopathic Pulmonary Fibrosis—FDA Review of Pirfenidone and Nintedanib. N Engl J Med 2015; 372:1189-1191 (Year: 2015).*

Wollin L, et. al. Mode of action of nintedanib in the treatment of idiopathic pulmonary fibrosis. Eur Respir J. May 2015;45(5):1434-45. (Year: 2015).*

Ottmann, O.G. et. al. Phase I dose-escalation trial investigating volasertib as monotherapy or in combination with cytarabine in patients with relapsed/refractory acute myeloid leukaemia. Br J Haematol. 2019. 184: 1018-1021. (Year: 2019).*

Lin, CC. et al. A phase I study of two dosing schedules of volasertib (BI 6727), an intravenous polo-like kinase inhibitor, in patients with advanced solid malignancies. Br J Cancer 110, 2434-2440 (2014). (Year: 2014).*

Doz, F, Locatelli, F, Baruchel, A, et al. Phase I dose-escalation study of volasertib in pediatric patients with acute leukemia or advanced solid tumors. Pediatr Blood Cancer. 2019; 66:e27900. (Year: 2019).*

Li Y, et. al. Severe lung fibrosis requires an invasive fibroblast phenotype regulated by hyaluronan and CD44. J Exp Med. Jul. 4, 2011;208(7):1459-71. (Year: 2011).*

(Continued)

*Primary Examiner* — Kamal A Saeed
*Assistant Examiner* — Quincy Mckoy
(74) *Attorney, Agent, or Firm* — ALGM LLP; Harry J. Guttman

(57) ABSTRACT

Disclosed herein are methods for treating an individual having, or at risk of having, pulmonary fibrosis, wherein volasertib, a salt thereof, or hydrate thereof, is administered to the individual in need thereof. In one aspect, the pulmonary fibrosis may be idiopathic pulmonary fibrosis. The volasertib may be administered in an amount and for a duration of time effective to achieve one or more outcomes selected from decreased invasiveness of pulmonary fibroblasts, increased clearance of myofibroblasts, decreased migration of pulmonary fibroblasts, decreased pulmonary fibroblast proliferation, decreased cell adhesion of pulmonary fibroblasts, decreased myofibroblast activation, decreased extracellular matrix (ECM) accumulation or production, and improved lung function.

17 Claims, 17 Drawing Sheets

(56) References Cited

OTHER PUBLICATIONS

Cai GQ, et. al. Downregulation of FAK-related non-kinase mediates the migratory phenotype of human fibrotic lung fibroblasts. Exp Cell Res. May 15, 2010;316(9):1600-9. (Year: 2010).*
Jiang, L., Li, Y., Yu, J. et al. A dry powder inhalable formulation of salvianolic acids for the treatment of pulmonary fibrosis: safety, lung deposition, and pharmacokinetic study. Drug Deliv. and Transl. Res. 11, 1958-1968 (2021). (Year: 2020).*
Bandiera, R., et al., "WT1 maintains adrenal-gonadal-primordium (AGP) identity and marks a novel population of AGP-like progenitors within the adult adrenal gland," Dev Cell, 2013, 27(1):5-18, 27 pgs.
Baughman, R.P., et al., "Overexpression of Transforming Growth Factor-α and Epidermal Growth Factor-receptor in Idiopathic Pulmonary Fibrosis," Sarcoidosis Vasc Diffuse Lung Dis, 1999, 16:57-61, 5 pgs.
Blackwell, T.S., et al., "Future Directions in Idiopathic Pulmonary Fibrosis Research: An NHLBI Workshop Report," Am J Respir Crit Care Med, 2014, 189(2):214-222, 9 pgs.
Bogdan, S., et al., "Epidermal growth factor receptor signaling," Curr Biol, 2001, 11(8):PR292-R295, 4 pgs.
Castriotta, R.J., et al., "Workshop on Idiopathic Pulmonary Fibrosis in Older Adults," Chest, 2010, 138(3):693-703, 11 pgs.
Chen, G., et al., "Foxa3 Induces Goblet Cell Metaplasia and Inhibits Innate Antiviral Immunity," Am J Respir Crit Care Med, 2014, 189(3):301-313, 13 pgs.
Chen, H., et al., "Targeting oncogenic Myc as a strategy for cancer treatment," Signal Transduct Target Ther, 2018, 3:5, 7 pgs.
Chen, J., et al., "ToppGene Suite for gene list enrichment analysis and candidate gene prioritization," Nucleic Acids Res, 2009, 37:W305-W311, 7 pgs.
Crystal, R.G., et al., "Future Research Directions in Idiopathic Pulmonary Fibrosis: Summary of a National Heart, Lung, and Blood Institute Working Group," Am J Respir Crit Care Med, 2002, 166:236-246, 11 pgs.
Crystal, R.G., et al., "Interstitial Lung Disease: Current Concepts of Pathogenesis, Staging and Therapy," Am J Med, 1981, 70:542-568, 27 pgs.
Da Silva, F., et al., "Identifying Direct Downstream Targets: WT1 ChIP-Seq Analysis," Chapter 15 in Nicolas Hastie (ed.), *The Wilms' Tumor (WT1) Gene: Methods and Protocols*, Meth Mol Biol, 2016, 1467:177-188, 12 pgs.
De Minicis, S., et al., "Role of endogenous opioids in modulating HSC activity in vitro and liver fibrosis in vivo," Gut, 2008, 57(3):352-364, 13 pgs.
Depianto, D.J., et al., "Heterogeneous gene expression signatures correspond to distinct lung pathologies and biomarkers of disease severity in idiopathic pulmonary fibrosis," Thorax, 2015, 70(1):48-56, 20 pgs.
Ebrahimkhani, M.R., et al., "Naltrexone, an opioid receptor antagonist, attenuates liver fibrosis in bile duct ligated rats," Gut, 2006, 55:1606-1616.
Gajjala, P.R., et al., "Notch 3: A New Culprit in Fibrotic Lung Disease," Am J Respir Cell Ma Bio, 2021, 64(4):403-404, 2 pgs.
Gebeshuber, C.A., et al., "Focal segmental glomerulosclerosis is induced by microRNA-193a and its downregulation of WT1," Nat Med, 2013, 19(4):481-487, 9 pgs.
Glasser, S.W., et al., "Mechanisms of Lung Fibrosis Resolution," Am J Pathol, 2016, 186(5):1066-1077, 12 pgs.
Glienke, W., et al., "Effective treatment of leukemic cell lines with wt1 siRNA," Leukemia, 2007, 21:2164-2170, 7 pgs.
Haak, A.J., et al., "Matrix Biomechanics and Dynamics in Pulmonary Fibrosis," Matrix Biol, 2018, 73:64-76, 21 pgs.
Hardie, W.D., et al., "EGF receptor tyrosine kinase inhibitors diminish transforming growth factor-α-induced pulmonary fibrosis," Am J Physiol Lung Cell Mol Physiol, 2008, 294:L1217-L1225, 9 pgs.
Hardie, W.D., et al., "Reversal of Lung Lesions in Transgenic Transforming Growth Factor α Mice by Expression of Mutant Epidermal Growth Factor Receptor," Am J Respir Cell Mol Biol, 1996, 15:499-508, 10 pgs.
Hardie, W.D., et al., "Genomic Profile of Matrix and Vasculature Remodeling in TGF-α-Induced Pulmonary Fibrosis," Am J Respir Cell Mol Biol, 2007, 37:309-321, 13 pgs.
Horowitz, J.C., et al., "Mechanisms for the Resolution of Organ Fibrosis," Physiology, 2019, 34:43-55, 13 pgs.
Hu, B., et al., "Mesenchymal Deficiency of Notch1 Attenuates Bleomycin-Induced Pulmonary Fibrosis," Am J Pathol, 2015, 185(11):3066-3075, 10 pgs.
Jorissen, R.N., et al., "Epidermal growth factor receptor: mechanisms of activation and signalling," Exp Cell Res, 2003, 284:31-53, 23 pgs.
Kasam, R.K., et al., "Fibrocyte accumulation in the lungs of cystic fibrosis patients," J Cystic Fibrosis, 2020, 19(5):815-822, 8 pgs.
Kasam, R.K., et al., "Inhibition of Aurora Kinase B attenuates fibroblast activation and pulmonary fibrosis," EMBO Mol Med, 2020, 12:e12131, 16 pgs.
Kasam, R.K., et al., "Dysregulation of Mesenchymal Cell Survival Pathways in Severe Fibrotic Lung Disease: The Effect of Nintedanib Therapy," Front Pharmacol, 2019, 10:532, 16 pgs.
Korfhagen, T.R., et al., "SAM-pointed domain ETS factor mediates epithelial cell-intrinsic innate immune signaling during airway mucous metaplasia," PNAS, 2012, 109(41):16630-16635, 6 pgs.
Korfhagen, T.R., et al., "Rapamycin Prevents Transforming Growth Factor-α-Induced Pulmonary Fibrosis," Am J Respir Cell Mol Biol, 2009, 41:562-572, 11 pgs.
Kramer, E.L., et al., "Subacute TGFβ expression drives inflammation, goblet cell hyperplasia, and pulmonary function abnormalities in mice with effects dependent on CFTR function," Am J Physiol Lung Cell Mol Physiol, 2018, 315(3):L456-L465, 10 pgs.
Kramer, E.L., et al., "Subacute TGFβ Exposure Drives Airway Hyperresponsiveness in Cystic Fibrosis Mice through the PI3K Pathway," Am J Respir Cell Mol Bio, 2020, 62(5):657-667, 11 pgs.
Luzina, I.G., et al., "Transcriptomic Evidence of Immune Activation in Macroscopically Normal-Appearing and Scarred Lung Tissues in Idiopathic Pulmonary Fibrosis," Cell Immunol, 2018, 325:1-13, 27 pgs.
Madala, S.K., et al., "Bone Marrow-Derived Stromal Cells Are Invasive and Hyperproliferative and Alter Transforming Growth Factor-α-Induced Pulmonary Fibrosis," Am J Respir Cell Mol Biol, 2014, 50(4):777-786, 10 pgs.
Madala, S.K., et al., "Dual Targeting of MEK and P13K Pathways Attenuates Established and Progressive Pulmonary Fibrosis," PloS One, 2014, 9(1):e86536, 11 pgs.
Madala, S.K., et al., "Inhibition of the avß6 integrin leads to limited alteration of TGF-α-induced pulmonary fibrosis," Am J Physiol Lung Cell Mol Physiol, 2014, 306:L726-L735, 10 pgs.
Madala, S.K., et al., "Matrix Metalloproteinase 12-Deficiency Augments Extracellular Matrix Degrading Metalloproteinases and Attenuates IL-13-Dependent Fibrosis," J Immunol, 2010, 184(7):3955-3963, 21 pgs.
Madala, S.K., et al., "MEK-ERK Pathway Modulation Ameliorates Pulmonary Fibrosis Associated with Epidermal Growth Factor Receptor Activation," Am J Respir Cell Mol Biol, 2012, 46(3):380-388, 9 pgs.
Madala, S.K., et al., "p70 ribosomal S6 kinase regulates subpleural fibrosis following transforming growth factor-α expression in the lung," Am J Physiol Lung Cell Mol Physiol, 2016, 310:L175-L186, 12 pgs.
Madala, S.K., et al., "Resistin-like molecule alphal (Fizzl) recruits lung dendritic cells without causing pulmonary fibrosis," Respir Res, 2012, 13:51, 10 pgs.
Madala, S.K., et al., "Unique and Redundant Functions of p70 Ribosomal S6 Kinase Isoforms Regulate Mesenchymal Cell Proliferation and Migration in Pulmonary Fibrosis," Am J Respir Cell Mol Biol, 2016, 55(6):792-803, 12 pgs.
Marlton, P., "The many facets of WT1 in acute myeloid leukemia: clarity remains elusive," Leukemia & Lymphoma, 2014, 55(2):235-237, 3 pgs.
Mckleroy, W., et al., "Always cleave up your mess: targeting collagen degradation to treat tissue fibrosis," Am J Physiol Lung Cell Mol Physiol, 2013, 304:L709-L721, 13 pgs.

(56) References Cited

OTHER PUBLICATIONS

Moens, C.B., et al., "Defects in heart and lung development in compound heterozygotes for two different targeted mutations at the N-myc locus," Development, 1993, 119:485-499, 15 pgs.
Noble, P.W., et al., "Pulmonary fibrosis: patterns and perpetrators," J Clin Invest, 2012, 122(8):2756-2762, 7 pgs.
Okubo, T., et al., "Nmyc plays an essential role during lung development as a dosage-sensitive regulator of progenitor cell proliferation and differentiation," Development, 2005, 132:1363-1374, 12 pgs.
Que, J., et al., "Mesothelium contributes to vascular smooth muscle and mesenchyme during lung development," PNAS, 2008, 105(43):16626-16630, 5 pgs.
Reddy, V.S., et al., "Extracellular small heat shock proteins: exosomal biogenesis and function," Cell Stress and Chaperones, 2018, 23(3):441-454, 14 pgs.
Redente, E.F., et al., "Persistent, Progressive Pulmonary Fibrosis and Epithelial Remodeling in Mice," Am J Respir Cell Mol Biol, 2021, 64(6):669-676, 8 pgs.
Reyfman, P.A., et al., "Single-Cell Transcriptomic Analysis of Human Lung Provides Insights into the Pathobiology of Pulmonary Fibrosis," Am J Respir Crit Care Med, 2019, 199(12):1517-1536, 20 pgs.
Richeldi, L., et al., "Efficacy and Safety of Nintedanib in Idiopathic Pulmonary Fibrosis," New Engl J Med, 2014, 370(22):2071-2082, 12 pgs.
Rong, Y., et al., "Wilms' Tumor 1 and Signal Transducers and Activators of Transcription 3 Synergistically Promote Cell Proliferation: A Possible Mechanism in Sporadic Wilms' Tumor," Cancer Res, 2006, 66(16):8049-8057, 9 pgs.
Rothaeusler, K., et al., "Assessment of Cell Proliferation by 5-Bromodeoxyuridine (BrdU) Labeling for Multicolor Flow Cytometry," Curr Protoc Cytom, 2007, 7.31.1-7.31.13, 13 pgs.
Ruiz-Perez, M.V., et al., "The MYCN Protein in Health and Disease," Genes, 2017, 8:113, 27 pgs.
Sawai, S., et al., "Defects of embryonic organogenesis resulting from targeted disruption of the N-myc gene in the mouse," Development, 1993, 117:1445-1455, 11 pgs.
Selman, M., et al., "Idiopathic Pulmonary Fibrosis: Prevailing and Evolving Hypotheses about Its Pathogenesis and Implications for Therapy," Ann Intern Med, 2001, 134:136-151, 16 pgs.
Selman, M., et al., "Idiopathic pulmonary fibrosis: misunderstandings between epithelial cells and fibroblasts?" Sarcoidosis Vasc Diffuse Lung Dis, 2004, 21:165-172, 8 pgs.
Singh, B., et al., "Repetitive intradermal bleomycin injections evokes T-helper cell 2 cytokine-driven pulmonary fibrosis," Am J Physiol Lung Cell Mol Physiol, 2017, 313(5):L796-L806, 11 pgs.
Sontake, V., et al., "New therapeutics based on emerging concepts in pulmonary fibrosis," Expert Opin Ther Targets, 2019, 23(1):69-81, 25 pgs.
Sontake, V., et al., "Wilms' tumor 1 drives fibroproliferation and myofibroblast transformation in severe fibrotic lung disease," JCI Insight, 2018, 3(16):e121252, 19 pgs.
Sontake, V., et al., "Fibrocytes Regulate Wilms' Tumor 1-Positive Cell Accumulation in Severe Fibrotic Lung Disease," J Immunol, 2015, 195(8):3978-3991, 32 pgs.
Sontake, V., et al., "Hsp90 regulation of fibroblast activation in pulmonary fibrosis," JCI Insight, 2017, 2(4):e91454, 19 pgs.
Tsukui, T., et al., "Collagen-producing lung cell atlas identifies multiple subsets with distinct localization and relevance to fibrosis," Nature Comms, 2020, 11:1920, 16 pgs.
Vicent, S., et al., "Wilms tumor 1 (WT1) regulates KRAS-driven oncogenesis and senescence in mouse and human models," J Clin Invest, 2010, 120(11):3940-3952, 13 pgs.
Von Gise, A., et al., "Contribution of Fetal, but Not Adult, Pulmonary Mesothelium to Mesenchymal Lineages in Lung Homeostasis and Fibrosis," Am J Respir Cell Mol Biol, 2016, 54(2):222-230, 9 pgs.
Wang, Y., et al., "Pan-transcriptome-based candidate therapeutic discovery for idiopathic pulmonary fibrosis," Ther Adv Respir Dis, 2020, 14:1-17, 17 pgs.
Wang, Y., et al., "Unsupervised gene expression analyses identify IPF-severity correlated signatures, associated genes and biomarkers," BMC Pulmonary Medicine, 2017, 17(1):133, 10 pgs.
Williams, R.M., et al., "Interpreting Second-Harmonic Generation Images of Collagen I Fibrils," Biophys J, 2005, 88:1377-1386, 10 pgs.
Wollin, L., et al., "Mode of action of nintedanib in the treatment of idiopathic pulmonary fibrosis," Eur Respir J, 2015, 45:1434-1445, 12 pgs.
Xiao, D., et al., "Polo-like Kinase-1 Regulates Myc Stabilization and Activates a Feedforward Circuit Promoting Tumor Cell Survival," Molecular Cell, 2016, 64:493-506, 15 pgs.
Yang, X., et al., "Reversal of myofibroblast differentiation: A review," Euro J Pharma, 2014, 734:83-90, 8 pgs.
Yombo, D.J.K., et al., "Heat shock protein 70 is a positive regulator of airway inflammation and goblet cell hyperplasia in a mouse model of allergic airway inflammation," J Biol Chem, 2019, 294(41):15082-15094, 13 pgs.
Yombo, D.J.K., et al., "The Protective Effects of IL-31RA Deficiency During Bleomycin-Induced Pulmonary Fibrosis," Front Immunol, 2021, 12:645717, 10 pgs.
Zhou, Y., et al., "Inhibition of mechanosensitive signaling in myofibroblasts ameliorates experimental pulmonary fibrosis," J Clin Invest, 2013, 123(3):1096-1108, 13 pgs.
Zoz, D.F., et al., "Idiopathic Pulmonary Fibrosis: A Disorder of Epithelial Cell Dysfunction," Am J Med Sci, 2011, 341(6):435-438, 9 pgs.
U.S. Appl. No. 62/630,866, filed Feb. 15, 2018, by: Madala et al., entitled: "Repurposing Barasertib for the Treatment Pulmonary Fibrosis."
U.S. Appl. No. 63/272,256, filed Oct. 27, 2021, by Madala et al., entitled: "Therapeutic Inhibition of the WT1-MYCN-PLK1 Axis and Pulmonary Fibrosis Using Volasertib."
Wen et al. (2015) "Targeting megakaryocytic-induced fibrosis in myeloproliferative neoplasms by AURKA inhibition" Nature Medicine, vol. 21, No. 12, pp. 1473-1480 (plus online methods).
White et al. (2013) "Inflammation, wound repair, and fibrosis: Reassessing the spectrum of tissue injury and resolution" J Pathol, vol. 229, No. 2, 141-144.
Woo et al. (2015) "Elucidating Compound Mechanism of Action by Network Perturbation Analysis" Cell, vol. 162, No. 2, pp. 441-451.
Wynn (2008) "Cellular and molecular mechanisms of fibrosis" J Pathol, vol. 214, No. 2, pp. 199-210.
Wynn et al. (2011) "Quantitative assessment of macrophage functions in repair and fibrosis" Curr Protoc Immunol, Chapter 14:Unit14.22 (15 pages).
Wynn et al. (2012) "Mechanisms of fibrosis: therapeutic translation for fibrotic disease" Nat Med, vol. 18, No. 7, pp. 1028-1040.
Xia et al. (2004) "Focal adhesion kinase is upstream of phosphatidylinositol 3-kinase/Akt in regulating fibroblast survival in response to contraction of type I collagen matrices via a beta 1 integrin viability signaling pathway" J Biol Chem, vol. 279, No. 31, pp. 33024-33034.
Yang et al. (2014) "Dual Aurora A and JAK2 kinase blockade effectively suppresses malignant transformation" Oncotarget, vol. 5, No. 10, pp. 2947-2961.
Zhang et al. (2001) "Vanadium stimulates human bronchial epithelial cells to produce heparin-binding epidermal growth factor-like growth factor: a mitogen for lung fibroblasts" Am J Respir Cell Mol Biol, vol. 24, pp. 123-131.
Zhang et al. (2018) "Cystic fibrosis transmembrane conductance regulator—emerging regulator of cancer" Cellular and Molecular Life Sciences, vol. 75, pp. 1737-1756.
Zhou et al. (2012) "Amphiregulin, an epidermal growth factor receptor ligand, plays an essential role in the pathogenesis of transforming growth factor-beta-induced pulmonary fibrosis" J Biol Chem, vol. 287, No. 50, pp. 41991-42000.
Raghu et al. (2006) "Incidence and prevalence of idiopathic pulmonary fibrosis" Am J Respir Crit Care Med, vol. 174, pp. 810-816.

(56) References Cited

OTHER PUBLICATIONS

Raghu et al. (2011) "An official ATS/ERS/JRS/ALAT statement: idiopathic pulmonary fibrosis: evidence-based guidelines for diagnosis and management" Am J Respir Crit Care Med, vol. 183, pp. 788-824.
Ramachandran et al. (2014) "A genomic signature approach to rescue DeltaF508-cystic fibrosis transmembrane conductance regulator biosynthesis and function" Am J Respir Cell Mol Biol, vol. 51, pp. 354-362.
Ramalingam et al. (2008) "Unique functions of the type II interleukin 4 receptor identified in mice lacking the interleukin 13 receptor alpha1 chain" Nat Immunol, vol. 9, No. 1, pp. 25-33.
Ramsey et al. (1999) "Intermittent administration of inhaled tobramycin in patients with cystic fibrosis" N Engl J Med, vol. 340, pp. 23-30.
Ratjen et al. (2002) "Matrix metalloproteases in BAL fluid of patients with cystic fibrosis and their modulation by treatment with dornase alpha" Thorax, vol. 57, pp. 930-934.
Ratjen et al. (2012) "Effect of azithromycin on systemic markers of inflammation in patients with cystic fibrosis uninfected with Pseudomonas aeruginosa" Chest, vol. 142, pp. 1259-1266.
Reddy et al. (2015) "Phase II study of saracatinib (AZD0530) in patients with previously treated metastatic colorectal cancer" Invest New Drugs, vol. 33, pp. 977-984.
Retsch-Bogart et al. (2009) "Efficacy and safety of inhaled aztreonam lysine for airway pseudomonas in cystic fibrosis" Chest, vol. 135, pp. 1223-1232.
Rimessi et al. (2015) "Mitochondrial Ca2+-dependent NLRP3 activation exacerbates the Pseudomonas aeruginosa—driven inflammatory response in cystic fibrosis" Nat Commun, vol. 6, Article 6201 (16 pages).
Ritchie et al. (2015) "limma powers differential expression analyses for RNA-sequencing and microarray studies" Nucleic Acids Res, vol. 43, No. 7, Article e47 (13 pages).
Rowe et al. (2013) "Optimizing nasal potential difference analysis for CFTR modulator development: assessment of ivacaftor in CF subjects with the G551D-CFTR mutation" PLoS One, vol. 8, No. 7, Article e66955 (8 pages).
Rowe et al. (2014) "Clinical mechanism of the cystic fibrosis transmembrane conductance regulator potentiator ivacaftor in G551D-mediated cystic fibrosis" Am J Respir Grit Care Med, vol. 190, pp. 175-184.
Sagel et al. (2005) "Induced sputum matrix metalloproteinase-9 correlates with lung function and airway inflammation in children with cystic fibrosis" Pediatr Pulmonol, vol. 39, pp. 224-232.
Sali et al. (1993) "Comparative protein modelling by satisfaction of spatial restraints" J Mol Biol, vol. 234, pp. 779-815.
Schneider et al. (2012) "Pleuropulmonary pathology in patients with rheumatic disease" Arch Pathol Lab Med, vol. 136, pp. 1242-1252.
Shannon et al. (2003) "Cytoscape: a software environment for integrated models of biomolecular interaction networks" Genome Res, vol. 13, pp. 2498-2504.
Sini et al. (2016) "Pharmacological Profile of BI 847325, an Orally Bioavailable, ATP-Competitive Inhibitor of MEK and Aurora Kinases" Mol Cancer Ther; vol. 15, No. 10, pp. 2388-2398 & Supplementary Figure S1.
Sirota et al. (2011) "Discovery and preclinical validation of drug indications using compendia of public gene expression data" Sci Transl Med, vol. 3, Article 96ra77 (22 pages).
Solomon et al. (2010) "An international randomized multicenter comparison of nasal potential difference techniques" Chest, vol. 138, pp. 919-928.
Spagnola et al. (2017) "Clinical trial research in focus: why do so many clinical trials fail in IPF?" Lancet Respir Med, vol. 5, No. 5, pp. 372-374.
Srikumar et al. (2016) "Potential Use of Flavopiridol in Treatment of Chronic Diseases" from Advances in Ex. Med. & Bio. Vol. 929, Drug Discovery from Mother Nature, Edited by Gupta et al. (Copyright 2016) Springer, Cham, Switzerland, pp. 209-228.
Stahlman et al. (1989) "Immunocytochemical localization of epidermal growth factor in the developing human respiratory system and in acute and chronic lung disease in the neonate" Lab Invest, vol. 60, No. 4, pp. 539-547.
Stanke et al. (2014) "The CF-modifying gene EHF promotes p.Phe508del-CFTR residual function by altering protein glycosylation and trafficking in epithelial cells" European journal of human genetics, vol. 22, pp. 660-666.
Stanton (2017) "Effects of Pseudomonas aeruginosa on CFTR chloride secretion and the host immune response" Am J Physiol Cell Physiol, vol. 312, pp. C357-C366.
Steele et al. (2013) "Molecular mechanisms in progressive idiopathic pulmonary fibrosis" Annu Rev Med, vol. 64, pp. 265-276.
Stoltz et al. (2010) "Cystic fibrosis pigs develop lung disease and exhibit defective bacterial eradication at birth" Sci Transl Med, vol. 2, Article 29ra31 (18 pages).
Strandjord et al. (1995) "Immunolocalization of transforming growth factor-alpha, epidermal growth factor (EGF), and EGF-receptor in normal and injured developing human lung" Pediatr Res, vol. 38, No. 6, pp. 851-856.
Subramanian et al. (2017) "A Next Generation Connectivity Map: L1000 Platform and the First 1,000,000 Profiles" Cell, vol. 171, No. 6, pp. 1437-1452.e17.
Sun et al. (2011) "New concepts of IL-10-induced lung fibrosis: fibrocyte recruitment and M2 activation in a CCL2/CCR2 axis" Am J Physiol Lung Cell Mol Physiol, vol. 300, pp. L341-L353.
Sun et al. (2022) "90% of drugs fail clinical trials - here's one way researchers can select better drug candidates" in The Conversation at https://theconversation.com/90-of-drugs-fail-clinical-trials-heres-one-way-researchers-can-select-better-drug-candidates-174152 (last accessed Dec. 26, 2024)(5 pages).
Sundberg et al. (2014) "Small-molecule screening identifies inhibition of salt-inducible kinases as a therapeutic strategy to enhance immunoregulatory functions of dendritic cells" Proc Natl Acad Sci U S A, vol. 111, No. 34, pp. 12468-12473.
Swigris et al. (2011) "Benefits of Pulmonary Rehabilitation in Idiopathic Pulmonary Fibrosis" Resp. Care, vol. 56, No. 6, pp. 783-789.
Thannickal et al. (2004) "Mechanisms of pulmonary fibrosis" Annu Rev Med, vol. 55, pp. 395-417.
Trepel et al. (2010) "Targeting the dynamic HSP90 complex in cancer" Nat Rev Cancer, vol. 10, No. 8, pp. 537-549.
Trzcinska-Daneluti et al. (2012) "Use of Kinase Inhibitors to Correct delta-F508-CFTR Function" Molecular & Cellular Proteomics 11.9, pp. 745-757. (plus supplemental material).
Tyler et al. (2007) "VX-680 inhibits Aurora A and Aurora B kinase activity in human cells" Cell Cycle, vol. 6, No. 22, pp. 2846-2854.
Varisco et al. (2016) "Excessive Reversal of Epidermal Growth Factor Receptor and Ephrin Signaling Following Tracheal Occlusion in Rabbit Model of Congenital Diaphragmatic Hernia" Mol Med, vol. 22, pp. 398-411.
Varone et al. (2017) "Investigational drugs for idiopathic pulmonary fibrosis" Expert Opinion on Investigational Drugs, vol. 26, No. 9, pp. 1019-1031.
Veit et al. (2014) "Some gating potentiators, including VX-770, diminish DeltaF508-CFTR functional expression" Science translational medicine, vol. 6, No. 246, Article 246ra97 (33 pages).
Verleden et al. (2017) "Chronic lung allograft dysfunction phenotypes and treatment" J Thorac Dis, vol. 9, No. 8, pp. 2650-2659.
Vermeer et al. (2003) "Segregation of receptor and ligand regulates activation of epithelial growth factor receptor" Nature, vol. 422, pp. 322-326.
Vertex Pharmaceuticals Inc. (2011) "Vertex and Cystic Fibrosis Foundation Therapeutics to Collaborate on Discovery and Development of New Medicines to Treat the Underlying Cause of Cystic Fibrosis" online at https://investors.vrtx.com/news-releases/news-release-details/vertex-and-cystic-fibrosis-foundation-therapeutics-collaborate. (Last accessed Dec. 20, 2024).
Vertex Pharmaceuticals Inc. (2016) "A Randomized, Double-Blind, Placebo-Controlled, Parallel-Group Study to Evaluate the Efficacy and Safety of VX-661 in Combination With Ivacaftor" oncline at: https://clinicaltrials.gov/study/NCT02347657?tab=history&a=9#version-content-panel). (Last accessed: Dec. 20, 2024).

(56) References Cited

OTHER PUBLICATIONS

Wainwright et al. (2015) "Lumacaftor-Ivacaftor in Patients with Cystic Fibrosis Homozygous for Phe508del CFTR" N Engl J Med, vol. 373, pp. 220-231.
Wang et al. (2003) "Epidermal growth factor receptor is a cellular receptor for human cytomegalovirus" Nature, vol. 424, pp. 456-461.
Wang et al. (2010) "STA-9090, a small-molecule Hsp90 inhibitor for the potential treatment of cancer" Current Opinion in Investigational Drugs, vol. 11, No. 12, pp. 1466-1476.
Wang et al. (2018) "PP-2, a src-kinase inhibitor, is a potential corrector for F508del-CFTR in cystic fibrosis" bioRxiv 288324; doi: https://doi.org/10.1101/288324 (42 pages).
Kannan et al. (2006) "Src kinase Lyn is crucial for Pseudomonas aeruginosa internalization into lung cells" Eur J Immunol, vol. 36, pp. 1739-1752.
Kaufman et al. (2015) "Fyn inhibition rescues established memory and synapse loss in Alzheimer mice" Ann Neural, vol. 77, pp. 953-971.
Kim et al. (2016) "PubChem Substance and Compound databases" Nucleic Acids Res, vol. 44, pp. D1202-D1213.
Kleaveland et al. (2014) "Fibrocytes are not an essential source of type I collagen during lung fibrosis" J Immunol, vol. 193, No. 10, pp. 5229-5239.
Kopeikin et al. (2014) "Combined effects of VX-770 and VX-809 on several functional abnormalities of F508del-CFTR channels" Journal of Cystic Fibrosis, vol. 13, pp. 508-514.
Kubiak et al. (1992) "Transforming growth factor-alpha gene expression in late-gestation fetal rat lung" Pediatr Res, vol. 31, No. 3, pp. 286-290.
Lamb (2007) "The Connectivity Map: a new tool for biomedical research" Nat Rev Cancer, vol. 7, pp. 54-60.
Lamb et al.(2006) "The Connectivity Map: using gene-expression signatures to connect small molecules, genes, and disease" Science, vol. 313, pp. 1929-1935.
Law et al. (2014) "voom: Precision weights unlock linear model analysis tools for RNA-seq read counts" Genome Biol, vol. 15, Article R29 (17 pages).
Le et al. (2014) "Blockade of IL-6 Trans Signaling Attenuates Pulmonary Fibrosis" J Immunol, vol. 193, pp. 3755-3768.
Lemjabbar et al. (2003) "Tobacco smoke-induced lung cell proliferation mediated by tumor necrosis factor alpha-converting enzyme and amphiregulin" J Biol Chem, vol. 278, No. 28, pp. 26202-26207.
Lepanto et al. (2011) "Pseudomonas aeruginosa interacts with epithelial cells rapidly forming aggregates that are internalized by a Lyn-dependent mechanism" Cell Microbiol, vol. 13, pp. 1212-1222.
Li et al. (2005) "Lysophosphatidic acid inhibits cholera toxin-induced secretory diarrhea through CFTR-dependent protein interactions" J Exp Med, vol. 202, pp. 975-986.
Li et al. (2007) "Spatiotemporal coupling of cAMP transporter to CFTR chloride channel function in the gut epithelia" Cell, vol. 131, pp. 940-951.
Liu et al. (2016) "Antitumor activity of TY-011 against gastric cancer by inhibiting Aurora A, Aurora B and VEGFR2 kinases" J Exp Clin Cancer Res., vol. 35, Article 183 (15 pages).
Lukacs et al. (2012) "CFTR: folding, misfolding and correcting the ~F508 conformational defect" Trends Mol Med, vol. 18, No. 2, pp. 81-91.
Madtes et al. (1988) "Induction of transforming growth factor-alpha in activated human alveolar macrophages" Cell, vol. 53, pp. 285-293.
Madtes et al. (1998) "Elevated transforming growth factor-alpha levels in bronchoalveolar lavage fluid of patients with acute respiratory distress syndrome" Am J Respir Crit Care Med, vol. 158, No. 2, pp. 424-430.
Maisonneuve et al. (2013) "Cancer Risk in Cystic Fibrosis: A 20-Year Nationwide Study From the United States" J Natl Cancer Inst, vol. 105, pp. 122-129.
Marshall et al. (2024) "The case of the missing mouse-developing cystic fibrosis drugs without using animals" Front Drug Discov, vol. 4, Article 1347246 (7 pages).
Mitra et al. (2005) "Focal adhesion kinase: in command and control of cell motility" Nat Rev Mol Cell Biol, vol. 6, pp. 56-68.
Moon et al. (2015) "Compartmentalized accumulation of cAMP near complexes of multidrug resistance protein 4 (MRP4) and cystic fibrosis transmembrane conductance regulator (CFTR) contributes to drug-induced diarrhea." J Biol Chem, vol. 290, pp. 11246-11257.
Moore et al. (2005) CCR2-mediated recruitment of fibrocytes to the alveolar space after fibrotic injury. Am J Pathol, vol. 166, No. 3, pp. 675-684.
Moore et al. (2013) "Animal models of fibrotic lung disease" Am J Respir Cell Mol Biol, vol. 49, No. 2, pp. 167-179.
Morris et al. (2009) "AutoDock4 and AutoDockTools4: Automated docking with selective receptor flexibility" J Comput Chem, vol. 30, pp. 2785-2791.
Muhlebach et al. (2016) "Biomarkers for cystic fibrosis drug development" J Cyst Fibros, vol. 15, pp. 714-723.
Nichols et al. (2008) "Anti-inflammatory therapies for cystic fibrosis-related lung disease" Clin Rev Allergy Immunol, vol. 35, pp. 135-153.
Nichols et al. (2015) "Inflammation and its genesis in cystic fibrosis" Pediatr Pulmonol, vol. 50, pp. S39-S56.
Nygaard et al. (2014) "Fyn kinase inhibition as a novel therapy for Alzheimer's disease" Alzheimers Res Ther, vol. 6, Article 8 (8 pages).
Nygaard et al. (2015) "A phase Ib multiple ascending dose study of the safety, tolerability, and central nervous system availability of AZD0530 (saracatinib) in Alzheimer's disease" Alzheimer's Research & Therapy, vol. 7, article 35 (11 pages).
Oermann et al. (2011) "Pseudomonas aeruginosa antibiotic susceptibility during long-term use of aztreonam for inhalation solution (AZLI)" J Antimicrob Chemother, vol. 66, pp. 2398-2404.
Ogilvie et al. (2011) "Differential global gene expression in cystic fibrosis nasal and bronchial epithelium" Genomics, vol. 98, pp. 327-336.
Olson et al. (2007) "Mortality from pulmonary fibrosis increased in the United States from 1992 to 2003" Am J Respir Crit Care Med, vol. 176, pp. 277-284.
O'Neal et al. (2015) "Gene expression in transformed lymphocytes reveals variation in endomembrane and HLA pathways modifying cystic fibrosis pulmonary phenotypes" Am J Hum Genet, vol. 96, pp. 318-328.
Ooms (2014) "The jsonlite Package: A Practical and Consistent Mapping Between JSON Data and R Objects" In arXiv e-prints at arXiv:403.2805 (29 pages).
O'Sullivan et al. (2011) "Health care utilization & costs for cystic fibrosis patients with pulmonary infections" Manag Care, vol. 20, pp. 37-44.
Panicker et al. (2015) "Fyn Kinase Regulates Microglial Neuroinflammatory Responses in Cell Culture and Animal Models of Parkinson's Disease" J Neurosci, vol. 35, pp. 10058-10077.
Pankow et al. (2015) "F508 Cftr interactome remodelling promotes rescue of cystic fibrosis" Nature, vol. 528, pp. 510-516.
Park et al. (2015) "Pathophysiological changes induced by Pseudomonas aeruginosa infection are involved in MMP-12 and MMP-13 upregulation in human carcinoma epithelial cells and a pneumonia mouse model" Infect Immun, vol. 83, pp. 4791-4799.
Park et al. (2016) "Type III Secretion System of Pseudomonas aeruginosa Affects Matrix Metalloproteinase 12 (MMP-12) and MMP-13 Expression via Nuclear Factor kB Signaling in Human Carcinoma Epithelial Cells and a Pneumonia Mouse Model" J Infect Dis, vol. 214, pp. 962-969.
Peschon et al. (1998) "An essential role for ectodomain shedding in mammalian development" Science, vol. 282, No. 5392, pp. 1281-1284.
Phuan et al. (2015) "Potentiators of Defective DeltaF508-CFTR Gating that Do Not Interfere with Corrector Action" Mol Pharmacol, vol. 88, pp. 791-799.
Pillai et al. (2014) "Heat shock protein 90 inhibitors in non-small-cell lung cancer" Curr Opin Oncol, vol. 26, No. 2, pp. 159-164.
Polosa et al. (1999) "Expression of c-erbB receptors and ligands in human bronchial mucosa" Am J Respir Cell Mol Biol, vol. 20, pp. 914-923.

(56) References Cited

OTHER PUBLICATIONS

Polosukhin et al. (2012) "Intratracheal bleomycin causes airway remodeling and airflow obstruction in mice" Exp Lung Res, vol. 38, No. 3, pp. 135-146.
Qu et al. (2009) "Inferring novel disease indications for known drugs by semantically linking drug action and disease mechanism relationships" BMC Bioinformatics, vol. 10, Suppl 5, Article S4 (16 pages).
Qu et al. (2012) "Applications of Connectivity Map in drug discovery and development" Drug Discov Today, vol. 17, pp. 1289-1298.
Qu et al. (2014) "Integrative clinical transcriptomics analyses for new therapeutic intervention strategies: a psoriasis case study" Drug Discov Today, vol. 19, pp. 1364-1371.
Dammann et al. (2003) "Role of neuregulin-1 beta in the developing lung" Am J Respir Crit Care Med, vol. 167, pp. 1711-1716.
Dar et al. (2010) "Aurora Kinase Inhibitors—Rising Stars in Cancer Therapeutics?" Mol Cancer Ther, vol. 9, No. 2, pp. 268-278.
De Santis et al. (2014) "Efficacy of aerosol therapy of lung cancer correlates with EGFR paralysis induced by AvidinOX-anchored biotinylated Cetuximab" Oncotarget, vol. 5, No. 19, pp. 9239-9255.
Dekkers et al. (2013) "A functional CFTR assay using primary cystic fibrosis intestinal organoids" Nature Medicine, vol. 19, pp. 939-945.
Dekkers et al. (2013) "Novel opportunities for CFTR-targeting drug development using organoids" Rare Dis, vol. 1, No. 1, Article e27112 (6 pages).
Dekkers et al. (2016) "Characterizing responses to CFTR-modulating drugs using rectal organoids derived from subjects with cystic fibrosis" Sci Transl Med, vol. 8, No. 344, Article 344ra84 (12 pages).
Dudley et al. (2011) "Computational repositioning of the anticonvulsant topiramate for inflammatory bowel disease" Sci Transl Med, vol. 3, No. 96, Article 96ra76 (12 pages).
Dunkelberger et al. (2010) "Complement and its role in innate and adaptive immune responses" Cell Res, vol. 20, pp. 34-50.
Elizur et al. (2008) "Airway inflammation in cystic fibrosis" Chest, vol. 133, pp. 489-495.
Eschenbrenner et al. (2013) "Role of JAK-STAT pathway in pulmonary fibrosis" Pneumologie, vol. 67, Article P06 (1 page).
Esen et al. (2001) "Invasion of human epithelial cells by Pseudomonas aeruginosa involves src-like tyrosine kinases p60Src and p59Fyn" Infect Immun, vol. 69, pp. 281-287.
Fancelli et al. (2006) "1,4,5,6-tetrahydropyrrolo[3,4-c]pyrazoles: identification of a potent Aurora kinase inhibitor with a favorable antitumor kinase inhibition profile" J. Med. Chem., vol. 49, No. 24, pp. 7247-7251.
Fernandes et al. (1999) "Production of epidermal growth factor related ligands in tumorigenic and benign human lung epithelial cells" Cancer Lett, vol. 142, pp. 55-63.
Fiorotto et al. (2016) "The cystic fibrosis transmembrane conductance regulator controls biliary epithelial inflammation and permeability by regulating Src tyrosine kinase activity" Hepatology, vol. 64, No. 6 , pp. 2118-2134.
Fiorotto et al. (2018) "Src kinase inhibition reduces inflammatory and cytoskeletal changes in ΔF508 human cholangiocytes and improves CFTR correctors efficacy" Hepatology, vol. 67, No. 3, pp. 972-988.
Floc'h et al. (2017) "Optimizing Therapeutic Effect of Aurora B Inhibition in Acute Myeloid Leukemia with AZD2811 Nanoparticles" Mol Cancer Ther, vol. 16, No. 6, pp. 1031-1040.
Gaggar et al. (2007) "Matrix metalloprotease-9 dysregulation in lower airway secretions of cystic fibrosis patients" Am J Physiol Lung Cell Mol Physiol, vol. 293, pp. L96-L104.
Gaggar et al. (2011) "The role of matrix metalloproteinases in cystic fibrosis lung disease" Eur Respir J, vol. 38, pp. 721-727.
Gajjala et al. (2023) "Wilms Tumor 1-Driven Fibroblast Activation and Subpleural Thickening in Idiopathic Pulmonary Fibrosis" Int J Mol Sci, vol. 24, Article 2850 (13 pages).
Gallucci et al. (2000) "TNF-alpha regulates transforming growth factor-alpha expression in regenerating murine liver and isolated hepatocytes" J Immunol, vol. 164, pp. 872-878.
Godl et al. (2005) "Proteomic characterization of the angiogenesis inhibitor SU6668 reveals multiple impacts on cellular kinase signaling" Cancer Res., vol. 65, No. 15 pp. 6919-6926.
Goldenson et al. (2015) "The aurora kinases in cell cycle and leukemia" Oncogene, vol. 34, No. 5, pp. 537-545.
Greene et al. (2015) "Understanding multicellular function and disease with human tissue-specific networks" Nat Genet, vol. 47, No. 6, pp. 569-576.
Gubens et al. (2015) "A phase II study of saracatinib (AZD0530), a Src inhibitor, administered orally daily to patients with advanced thymic malignancies" Lung Cancer, vol. 89, No. 1, pp. 57-60.
Guo et al. (2014) "CD24 activates the NLRP3 inflammasome through c-Src kinase activity in a model of the lining epithelium of inflamed periodontal tissues" Immun Inflamm Dis, vol. 2, pp. 239-253.
Hamada et al. (2005) "Anti-vascular endothelial growth factor gene therapy attenuates lung injury and fibrosis in mice" J Immunol, vol. 175, pp. 1224-1231.
Hannon et al. (2010) "Effects of the Src Kinase Inhibitor Saracatinib (AZD0530) on Bone Turnover in Healthy Men: A Randomized, Double-Blind, Placebo-Controlled, Multiple-Ascending-Dose Phase I Trial" Journal of Bone and Mineral Research, vol. 25, No. 3, pp. 463-471.
Hannon et al. (2012) "Effects of Src kinase inhibition by saracatinib (AZD0530) on bone turnover in advanced malignancy in a Phase I study" Bone, vol. 50, No. 4, pp. 885-892.
Hardie et al. (1999) "Immunolocalization of transforming growth factor alpha and epidermal growth factor receptor in lungs of patients with cystic fibrosis" Pediatr Dev Pathol,, vol. 2, No. 5, pp. 415-423.
Hardie et al. (2004) "Conditional expression of transforming growth factor-alpha in adult mouse lung causes pulmonary fibrosis" Am J Physiol Lung Cell Mol Physiol, vol. 286, pp. L741-L749.
Hardie et al. (2010) "Signaling pathways in the epithelial origins of pulmonary fibrosis" Cell Cycle, vol. 9, No. 14, pp. 2769-2776.
Hecht (2000) "Bleomycin: new perspectives on the mechanism of action" J Nat Prod, vol. 63, pp. 158-168.
Helfrich et al. (2016) "Barasertib (AZD1152), a Small Molecule Aurora B Inhibitor, Inhibits the Growth of SCLC Cell Lines In Vitro and In Vivo" Mol Cancer Ther, vol. 15, No. 10, pp. 2314-2322.
Hennequin et al. (2006) N-(5-chloro-1,3-benzodioxol-4-yl)-7-[2-(4-methylpiperazin-1-yl)ethoxy]-5-(tetrahydro-2H- pyran-4-yloxy)quinazolin-4-amine, a novel, highly selective, orally available, dual-specific c-Src/Abl kinase inhibitor J. Med. Chem. vol. 49, No. 22, pp. 6465-6488.
Hou et al (2016) "Emerging role of cystic fibrosis transmembrane conductance regulator—an epithelial chloride channel in gastrointestinal cancers" World J Gastrointest Oncol, vol. 8, No. 3, pp. 282-288.
Howard et al. (2009) "Fragment-based discovery of the pyrazol-4-yl urea (AT9283), a multitargeted kinase inhibitor with potent aurora kinase activity" J Med Chem, vol. 52, No. 2, pp. 379-388.
Hoyle et al. (1999) "Emphysematous lesions, inflammation, and fibrosis in the lungs of transgenic mice overexpressing platelet-derived growth factor" Am J Pathol, vol. 154, No. 6, pp. 1763-1775.
Hu et al. (2009) "Human disease-drug network based on genomic expression profiles" PLoS One, vol. 4, No. 8, Article e6536 (11 pages).
Hutchison et al. (2013) "Resident mesenchymal cells and fibrosis" Biochim Biophys Acta, vol. 1832, No. 7, pp. 962-971.
Tannitti et al. (2016) "IL-1 receptor antagonist ameliorates inflammasome-dependent inflammation in murine and human cystic fibrosis" Nat Commun, vol. 7, Article 10791 (16 pages).
Ibrahim et al. (2015) "Inhalation drug delivery devices: technology update" Medical Devices: Evidence and Research, vol. 8, pp. 131-139.
Inoue et al. (2002) "Basic fibroblast growth factor and its receptors in idiopathic pulmonary fibrosis and lymphangioleiomyomatosis" Am J Respir Crit Care Med, vol. 166, pp. 765-773.

(56) References Cited

OTHER PUBLICATIONS

Torio et al. (2010) "Discovery of drug mode of action and drug repositioning from transcriptional responses" Proc Natl Acad Sci U S A, vol. 107, pp. 14621-14626.
Torio et al. (2010) "Identification of small molecules enhancing autophagic function from drug network analysis" Autophagy, vol. 6, pp. 1204-1205.
Jakubzick et al. (2004) "Augmented pulmonary IL-4 and IL-13 receptor subunit expression in idiopathic interstitial pneumonia" J Clin Pathol, vol. 57, pp. 477-486.
Jenkins et al. (2017) "An Official American Thoracic Society Workshop Report: Use of Animal Models for the Preclinical Assessment of Potential Therapies for Pulmonary Fibrosis" Am J Respir Cell Mol Biol, vol. 56, No. 5, pp. 667-679.
Jetton et al. (2009) "The cell cycle as a therapeutic target against Trypanosoma brucei: Hesperadin inhibits Aurora kinase-1 and blocks mitotic progression in bloodstream forms" Molecular Microbiology, vol. 72, No. 2 pp. 442-458.
CN104906120A English-language translation, 2015 (12 pages).
International Search Report from PCT/US2019/017917, mailed May 15, 2019, 3 pages.
Written Opinion from PCT/US2019/017917, mailed May 15, 2019, 4 pages.
International Search Report from PCT/US2018/033780, mailed Aug. 7, 2018, 3 pages.
Written Opinion from PCT/US2018/033780, mailed Aug. 7, 2018, 5 pages.
Restriction Requirement in U.S. Appl. No. 16/614,356 dated Jun. 1, 2021, 8 pages.
Response to Restriction Requirement in U.S. Appl. No. 16/614,356 dated Jul. 23, 2021, 5 pages.
Non final Office action in U.S. Appl. No. 16/614,356 dated Aug. 18, 2021, 30 pages.
Restriction Requirement in U.S. Appl. No. 16/967,441 dated Dec. 22, 2021, 9 pages.
Response to Restriction Requirement in U.S. Appl. No. 16/967,441 dated Feb. 21, 2022, 4 pages.
NonFinal Office action in U.S. Appl. No. 16/967,441 dated Apr. 18, 2022, 44 pages.
Response to non final Office action in U.S. Appl. No. 16/967,441 dated Jul. 27, 2022, 21 pages.
Final Office Action in U.S. Appl. No. 16/967,441 dated Oct. 20, 2022, 25 pages.
Request for Continued Examination and Response to Final Office action in U.S. Appl. No. 16/967,441 dated Jan. 15, 2023, 15 pages.
NonFinal Office action in U.S. Appl. No. 16/967,441 dated Apr. 3, 2023, 15 pages.
Response to non final Office action in U.S. Appl. No. 16/967,441 dated Jun. 22, 2023, 20 pages.
Final Office action in U.S. Appl. No. 16/967,441 dated Aug. 22, 2023, 15 pages.
Request for Continued Examination and Response to Final Office action in U.S. Appl. No. 16/967,441 dated Feb. 16, 2024, 20 pages.
Nonfinal Office action in U.S. Appl. No. 16/967,441 dated Jun. 27, 2024, 19 pages.
Response to non final Office action in U.S. Appl. No. 16/967,441 dated Sep. 8, 2024, 20 pages.
Final Office action in U.S. Appl. No. 16/967,441 dated Oct. 11, 2024, 11 pages.
Request for Continued Examination and Response to Final Office action in U.S. Appl. No. 16/967,441 dated Dec. 31, 2024,18 pages.
Nonfinal Office action in U.S. Appl. No. 17/650,846 dated Sep. 11, 2024, 41 pages.
Response to Nonfinal Office action in U.S. Appl. No. 17/650,846 dated Jan. 21, 2025, 18 pages.
Abraham et al. (2017) "Cystic Fibrosis & disorders of the large intestine: DIOS, constipation, and colorectal cancer" Journal of Cystic Fibrosis, vol. 16, pp. S40-S49.
Accurso et al. (2010) "Effect of VX-770 in persons with cystic fibrosis and the G551D-CFTR mutation" N Engl J Med, vol. 363, pp. 1991-2003.
Ahluwalia et al. (2014) "New therapeutic targets in idiopathic pulmonary fibrosis. Aiming to rein in runaway wound-healing responses" Am J Respir Crit Care Med, vol. 190, No. 8, pp. 867-878.
Ahmad et al. (2009) "Exhaled nitric oxide estimation by a simple and efficient noninvasive technique and its utility as a marker of airway inflammation in mice" J Appl Physiol, vol. 107, pp. 295-301.
Barrett et al. (2007) "NCBI GEO: mining tens of millions of expression profiles—database and tools update" Nucleic Acids Res, vol. 35: pp. D760-D765.
Barshir et al. (2013) "The TissueNet database of human tissue protein-protein interactions" Nucleic Acids Res, vol. 41, pp. D841-D844.
Barshir et al. (2014) "Comparative analysis of human tissue interactomes reveals factors leading to tissue-specific manifestation of hereditary diseases" PLoS Comput Biol, vol. 10, No. 6, Article 1003632 (12 pages).
Baselga el al. (2010) "Phase I Safety, Pharmacokinetics, and Inhibition of Src Activity Study of Saracatinib in Patients with Solid Tumors" Clin Cancer Res, vol. 16, No. 19, pp. 4876-4883.
Bavetsias et al. (2012) "Optimization of imidazo[4,5-b]pyridine-based kinase inhibitors: identification of a dual FLT3/Aurora kinase inhibitor as an orally bioavailable preclinical development candidate for the treatment of acute myeloid leukemia" J Med Chem, vol. 55, pp. 8721-8734.
Bayliss et al. (2012) "On the molecular mechanisms of mitotic kinase activation" Open Biol, vol. 2, Article 120136 (20 pages).
Bhagirath et al. (2016) "Cystic fibrosis lung environment and Pseudomonas aeruginosa infection" BMC Pulm Med, vol. 16, Article 174 (22 pages).
Bjoraker et al. (1998) "Prognostic Significance of Histopathologic Subsets in Idiopathic Pulmonary Fibrosis" Am J Respir Crit Care Med, vol. 157, pp. 199-203.
Booth et al. (2001) "Interleukin-13 induces proliferation of human airway epithelial cells in vitro via a mechanism mediated by transforming growth factor-alpha" Am J Respir Cell Mol Biol, vol. 25, pp. 739-743.
Boss et al. (2009) "Clinical Experience with Aurora Kinase Inhibitors: A Review" The Oncologist, vol. 14, pp. 780-793.
Boyle et al. (2014) "A CFTR corrector (lumacaftor) and a CFTR potentiator (ivacaftor) for treatment of patients with cystic fibrosis who have a phe508del CFTR mutation: a phase 2 randomised controlled trial" Lancet Respir Med, vol. 2, pp. 527-538.
Brandvold et al. (2012) "Development of a Highly Selective c-Src Kinase Inhibitor" ACS Chem Biol., vol. 7, No. 8, pp. 1393-1398.
Chapman (2011) "Epithelial-mesenchymal interactions in pulmonary fibrosis" Annu Rev Physiol, vol. 73, pp. 413-435.
Cheng et al. (2014) "Systematic evaluation of connectivity map for disease indications" Genome Med, vol. 6, Article 95 (8 pages).
Chmiel et al. (2013) "Antibiotic and anti-inflammatory therapies for cystic fibrosis" Cold Spring Harb Perspect Med, vol. 3, Article a009779 (17 pages).
Cholon et al. (2014) "Potentiator ivacaftor abrogates pharmacological correction of DeltaF508 CFTR in cystic fibrosis" Sci Transl Med, vol. 6, No. 246, pp. 246ra96 (31 pages).
Clancy (2014) "CFTR potentiators: not an open and shut case" Sci Transl Med, vol. 6, No. 246, Article 246fs27 (3 pages).
Clancy et al. (2013) "Multicenter intestinal current measurements in rectal biopsies from CF and non-CF subjects to monitor CFTR function" PloS One, vol. 8, No. 9, Article e73905 (13 pages).
Cool et al. (2006) "Fibroblast foci are not discrete sites of lung injury or repair: the fibroblast reticulum" Am J Respir Crit Care Med, vol. 174, pp. 654-658.
Copiz et al. (2016) "c- Src and its role in cystic fibrosis" Eur J Cell Biol, vol. 95, pp. 401-413.
Dalton et al. (2012) "New model of cystic fibrosis transmembrane conductance regulator proposes active channel-like conformation" J Chem Inf Model, vol. 52, pp. 1842-1853.

* cited by examiner

METHODS AND COMPOSITIONS FOR THE TREATMENT OF PULMONARY FIBROSIS USING VOLASERTIB

CROSS-REFERENCE TO RELATED APPLICATIONS

This application claims priority to and benefit of U.S. Provisional Application Ser. No. 63/272,256, filed Oct. 27, 2021, entitled "Therapeutic Inhibition of the WT1-MYCN-PLK1 Axis and Pulmonary Fibrosis Using Volasertib," the contents of which is incorporated in its entirety for all purposes.

STATEMENT REGARDING FEDERALLY-SPONSORED RESEARCH

This invention was made with government support under W81XWH-17-1-0666 awarded by the Defense Advanced Research Projects Agency, and HL134801 awarded by the National Institutes of Health. The government has certain rights in the invention.

BACKGROUND

Pulmonary fibrosis is the final common pathway of several aging-associated chronic lung diseases that are associated with excessive fibroproliferation, survival, and deposition of the extracellular matrix (ECM) in the lung parenchyma. With aging, fibrosis occurs in both idiopathic pneumonia and systemic connective-tissue diseases. Idiopathic Pulmonary Fibrosis (IPF) is perhaps the most pernicious and enigmatic form of lung fibrosis and recent evidence indicates that the prevalence of this disease is increasing in the U.S. and around the world. The advent of two FDA-approved therapies for IPF has energized the field, but enthusiasm is tempered by the recognition that their side effect profiles are formidable and their effects are suppressive rather than remission-inducing or curative. New and better drugs for treatment of pulmonary fibrosis are needed.

BRIEF SUMMARY

Disclosed herein are methods for treating an individual having, or at risk of having, pulmonary fibrosis, wherein volasertib, a salt thereof, or hydrate thereof, is administered to the individual in need thereof. In one aspect, the pulmonary fibrosis may be idiopathic pulmonary fibrosis. The volasertib may be administered in an amount and for a duration of time effective to achieve one or more outcomes selected from decreased invasiveness of pulmonary fibroblasts, increased clearance of myofibroblasts, decreased migration of pulmonary fibroblasts, decreased pulmonary fibroblast proliferation, decreased cell adhesion of pulmonary fibroblasts, decreased myofibroblast activation, decreased extracellular matrix (ECM) accumulation or production, and improved lung function.

BRIEF DESCRIPTION OF THE DRAWINGS

Those of skill in the art will understand that the drawings, described below, are for illustrative purposes only. The drawings are not intended to limit the scope of the present teachings in any way.

Figure 1:
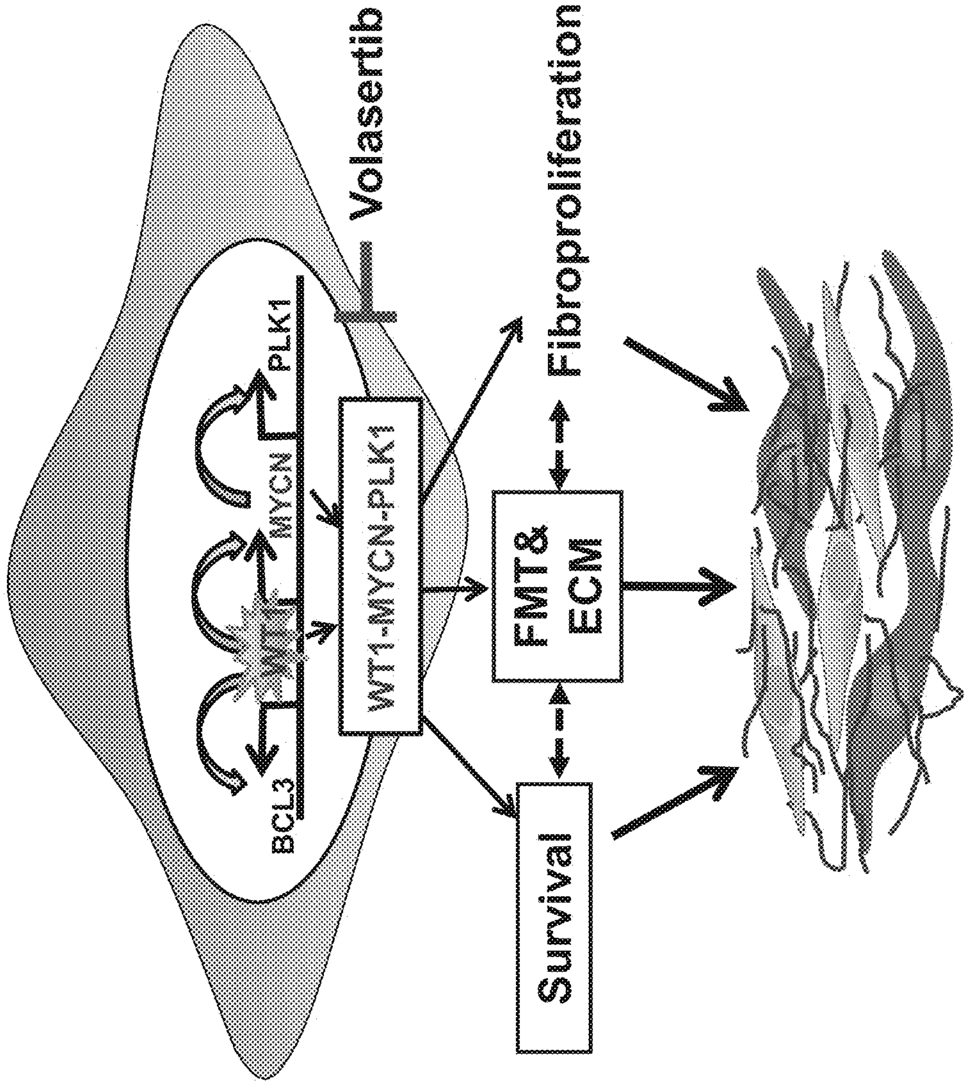
FIG. 1. Volasertib therapy inhibits the WT1-MYCN-PLK1 axis to attenuate fibroblast activation including fibroproliferation, survival, and ECM production.

MYCN-positive fibroblasts accumulate in the distal areas of IPF Lungs. Top Panels: Normal lung shown at low (Scale bar, 500 μm) and high magnification (Scale bar, 50 μm). Bottom Panels: Spindle-shaped nuclei of MYCN-positive fibroblasts indicated using arrows in high magnification images of subpleura and fibrotic foci of IPF lung. Scale Bar, 50 μm.

DETAILED DESCRIPTION

Definitions

Unless otherwise noted, terms are to be understood according to conventional usage by those of ordinary skill in the relevant art. In case of conflict, the present document, including definitions, will control. Preferred methods and materials are described below, although methods and materials similar or equivalent to those described herein may be used in practice or testing of the present invention. All publications, patent applications, patents and other references mentioned herein are incorporated by reference in their entirety. The materials, methods, and examples disclosed herein are illustrative only and not intended to be limiting.

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" may mean within 1 or more than 1 standard deviation, per the practice in the art. Alternatively, "about" may mean a range of up to 20%, or up to 10%, or up to 5%, or up to 1% of a given value. Alternatively, particularly with respect to biological systems or processes, the term may mean within an order of magnitude, preferably within 5-fold, and more preferably within 2-fold, of a value. Where particular values are described in the application and claims, unless otherwise stated the term "about" meaning within an acceptable error range for the particular value should be assumed.

As used herein, the term "effective amount" means the amount of one or more active components that is sufficient to show a desired effect. This includes both therapeutic and prophylactic effects. When applied to an individual active ingredient, administered alone, the term refers to that ingredient alone. When applied to a combination, the term refers to combined amounts of the active ingredients that result in the therapeutic effect, whether administered in combination, serially or simultaneously. The term "effective amount," is used herein to include the amount of a therapeutic agent that, when administered to a patient for treating a subject having pulmonary fibrosis, is sufficient to effect treatment of the disease (e.g., by diminishing, ameliorating or maintaining the existing disease or one or more symptoms of disease or its related comorbidities).

The terms "individual," "host," "subject," and "patient" are used interchangeably to refer to an animal that is the object of treatment, observation and/or experiment. Generally, the term refers to a human patient, but the methods and compositions may be equally applicable to non-human subjects such as other mammals. In some aspects, the terms refer to humans. In further aspects, the terms may refer to children.

The term "lung function" is used herein to refer to a measure of how well the lung is working. Lung function tests include, but are not limited to, spirometry, pulse oximetry, exercise stress test or arterial blood gas test. Hydroxyproline levels, lung density and total cell count in bronchoalveolar lavage fluid may also be used to assess lung function.

The term "salt(s)", as employed herein, denotes acidic and/or basic salts formed with inorganic and/or organic acids and bases. In addition, when an active agent contains both a basic moiety, such as, but not limited to an amine or a pyridine or imidazole ring, and an acidic moiety, such as, but not limited to a carboxylic acid, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps, which may be employed during preparation. Salts of the compounds of the active agent may be formed, for example, by reacting a compound of the active agent with an amount of acid or base, such as an equivalent amount, in a medium such as one in which the salt precipitates or in an aqueous medium followed by lyophilization. When the compounds are in the forms of salts, they may comprise pharmaceutically acceptable salts. Such salts may include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. The active agent may form salts, which are also within the scope of the preferred aspects. Reference to a compound of the active agent herein is understood to include reference to salts thereof, unless otherwise indicated.

Pulmonary fibrosis is a general term used to describe an increased accumulation of extracellular matrix ("ECM") in the distal lung, rendering the lung stiff and compromising its ability to facilitate normal gas exchange. Patients typically present with the insidious onset of shortness of breath with exertion as the disease often goes unnoticed in its early stages. Pulmonary fibrosis can be associated with a number of underlying diseases (such as connective tissue/rheumatologic disease) or environmental exposures (asbestosis), or it can be idiopathic, i.e., of unknown cause, in nature. Progressive tissue fibrosis is a major cause of morbidity, and idiopathic pulmonary fibrosis (IPF) is a terminal illness characterized by unremitting ECM deposition in the lung with very limited choice of therapies. [See U.S. Pat. No. 10,973,882.]

Disclosed herein are methods and compositions for the treatment of pulmonary fibrosis. In one aspect, the method may comprise administering volasertib (or a salt or hydrate thereof) to an individual having, or at risk, of having, pulmonary fibrosis. In one aspect, the pulmonary fibrosis may be idiopathic pulmonary fibrosis.

Volasertib, N-[trans-4-[4-(cyclopropylmethyl)-1-piperazinyl]cyclohexyl]-4-[[(7R)-7-ethyl-5,6,7,8-tetrahydro-5-methyl-8-(1-methylethyl)-6-oxo-2-pteridinyl]amino]-3-methoxy-benzamide (Molecular Weight: 618.81) has the following chemical structure:

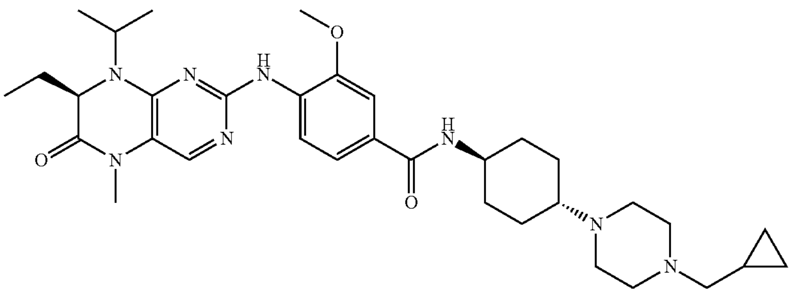 [SMILES: CC[C@@H]1C(=O)N(C)c2cnc(Nc3ccc(C(=O)N[C@H]4CC[C@H](N5CCN(CC6CC6)CC5)CC4)cc3OC)nc2N1C(C)C]

In one aspect, the administration may comprise administration of a dose of volasertib (or salt or hydrate thereof) in an amount of about 250, about 300, about 350, about 400, about 450 or about 500 mg. In some aspects, the administration may comprise administering a dose of volasertib (or salt or hydrate thereof) in an amount of from about 1 mg or less to about 1,000 mg or more, for example, from about 10, about 20, about 30, about 40, about 50, about 60, about 70, about 80, about 90, or about 100 mg to about 150, about 200, about 250, about 300, about 350, about 400, about 450, about 500, about 550, about 600, about 650, about 700, about 750, about 800, or about 900 mg. In some aspects, the volasertib (or salt or hydrate thereof) may be provided in a range of dosages to permit divided dosages to be administered.

In one aspect, for example via intravenous administration, volasertib (or salt or hydrate thereof) may be administered in a daily dose of 250 to 500 mg during a 4 week treatment cycle. In one aspect, the administration may be intravenously, wherein the volasertib may be administered to an individual in need thereof a daily dose of about 200 to about 500 mg. In another aspect, the dose may be about 200, about 250, about 300, about 350, about 400, about 450 or about 500 mg. In a further aspect, the dose may be about 300 or about 350 mg. In one aspect, volasertib (or salt or hydrate thereof) may be administered as a slow intravenous infusion over several hours, e.g., over about 1, about 2, about 4, about 6, about 10, about 12 or about 24 hours. In one aspect, volasertib may administered at an interval selected from twice a day, three times a day, daily, every other day, every three days, every four days, every five days, every six days, weekly, every two weeks, every three weeks, and monthly.

In one aspect, the administering may be in an amount and for a duration of time effective to attenuate fibrosis progression associated with pulmonary fibrosis. In one aspect, the administering may be in an amount and for a duration of time effective to achieve one or more outcomes selected from decreased invasiveness of pulmonary fibroblasts, increased clearance of myofibroblasts, decreased migration of pulmonary fibroblasts, decreased pulmonary fibroblast proliferation, decreased cell adhesion of pulmonary fibroblasts, decreased myofibroblast activation, decreased extracellular matrix (ECM) accumulation or production, and improved lung function. Improvement of lung function may be determined by one or more of spirometry, pulse oximetry, exercise stress test or arterial blood gas test. In one aspect, the administration is effective to reduce a symptom of pulmonary fibrosis compared to an untreated control.

In one aspect, the method may comprise administration of a second agent (or co-active) to the individual in need thereof. In this aspect, the second agent may be one or more of nintedanib, pirfenidone, tocilizumab, nivolumab, pembrolizumab, pidilizumab, lambrolizumab, atezolizumab, durvalumab, avelumab, ofnivolumab, and ipilmumab. The second agent may be administered at a time period selected from prior to said volasertib administration, during said volasertib administration, or following said volasertib administration. In certain aspects two or more therapeutic agents may be incorporated to be administered into a single tablet or other dosage form (e.g., in a combination therapy); however, in other aspects the therapeutic agents may be provided in separate dosage forms.

In one aspect, the administration may comprise a loading dose. For example, the method may comprise administering a loading dose of volasertib and administering one or more maintenance doses of volasertib, wherein each of the loading dose and the maintenance doses are administered in an amount that together are sufficient to treat pulmonary fibrosis. For example, the loading dose may be administered by injection (e.g., subcutaneously) or orally followed by maintenance dosing administered orally, intravenously, nasally, subcutaneously, transdermally, or via pulmonary administration. In one aspect, the loading dose may be intravenously administered. For example, the intravenously (e.g., as a bolus or infusion) administered loading-dose may be administered in an amount sufficient to produce a mean steady-state concentration of the volasertib in plasma.

In one aspect, the administration may comprise a loading dose and a maintenance dose. The maintenance dose may be administered in an amount and frequency sufficient to maintain a desired level of the medication in the blood. In one aspect, the administration may comprise a loading dose and a maintenance dose, wherein said loading dose is larger than said maintenance dose. In one aspect, a maintenance dose may be administered, for example, at a rate of from once per week to three times daily (e.g., once per every 5-7 days, once per every 3 days, every other day, once daily, twice daily, or three times daily).

In one aspect, the individual in need of treatment may be an adult. In one aspect, the individual may be under 18 years of age, or less than 16, 15, 14, 13, 12, 11, 10, 9, 8, 7, 6, 5, 4, 3, 2, or 1 year of age. In one aspect, the individual may be pre-pubescent.

The administration method may take a variety of different forms. For example, the administration route may be selected from one or more of oral, parenteral, intravenous, subcutaneous, and via pulmonary delivery, or inhalation.

Pharmaceutical Compositions

The disclosed actives may be administered in a dosage form, for example, a unit dosage forms for oral administration such as tablets and capsules. Unit dosage forms may be configured for administration once a day, twice a day, or more. The pharmaceutical compositions may be isotonic with the blood or other body fluid of the recipient. Isotonicity may be attained using sodium tartrate, propylene glycol or other inorganic or organic solutes, for example, sodium chloride. The compositions may employ buffering agents such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles may include fluid and nutrient replenishers, electrolyte replenishers (such as those based on Ringer's dextrose), and the like.

The compositions may employ a pharmaceutically acceptable preservative to increase the shelf life of the pharmaceutical compositions, for example, benzyl alcohol parabens, thimerosal, chlorobutanol, or benzalkonium chloride may be employed. Preservative may be present in an amount of from about 0.02% to about 2% based on the total weight of the composition, although larger or smaller amounts may be desirable depending upon the agent selected. Reducing agents, as described above, may be advantageously used to improve shelf life of the formulation. The active may be provided in an admixture with a suitable carrier, diluent, or excipient such as sterile water, physiological saline, glucose, or the like, and may contain auxiliary substances such as wetting or emulsifying agents, pH buffering agents, gelling or viscosity enhancing additives, preservatives, flavoring agents, colors, and the like, depending upon the route of administration and the preparation desired. Such preparations may include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Lipids that may be used for liposomal formulation may include, monoglycerides, diglycerides, sulfatides, lysolecithin, phospholipids, saponin, bile acids, and the like. The presence of such additional components may influence the physical state, solubility, stability, rate of in vivo release, and rate of in vivo clearance, and are thus may be chosen according to the intended application and the selected route of administration.

When administered as a dosage form, the dose may comprise from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Pulmonary delivery of the active agent may also be employed. The active agent may be delivered to the lungs while inhaling and traverses across the lung epithelial lining to the blood stream. A wide range of mechanical devices designed for pulmonary delivery of therapeutic products may be employed, including but not limited to nebulizers, metered dose inhalers, and powder inhalers, which may be used to deliver formulations suitable for the dispensing of active agent.

EXAMPLES

The following non-limiting examples are provided to further illustrate aspects of the invention disclosed herein. It should be appreciated by those of skill in the art that the techniques disclosed in the examples that follow represent approaches that have been found to function well in the practice of the invention, and thus may be considered to constitute examples of modes for its practice. However, those of skill in the art should, in light of the present disclosure, appreciate that many changes may be made in the specific aspects that are disclosed and still obtain a like or similar result without departing from the spirit and scope of the invention.

A key pathologic process in pulmonary fibrosis is fibroblast activation, which includes fibroproliferation, fibroblast-to-myofibroblast transformation (FMT), and impaired apoptotic clearance of myofibroblasts. These processes collectively result in excessive extracellular matrix (ECM) production, and the formation of scar tissue. Aberrant activation of Wilms' Tumor 1 (WT1), a novel zinc-finger transcription factor, appears to drive fibroblast activation and ECM deposition in idiopathic pulmonary fibrosis (IPF), a fatal fibrotic lung disease. Wilms' Tumor 1 (WT1) is upregulated in fibroblasts of IPF lungs and mouse models of pulmonary fibrosis. WT1 functions as a positive regulator of fibroproliferation, FMT and ECM production. Integrative analysis of ChIP seq and RNA-seq data has identified novel gene targets of WT1 involved in fibroblast activation, and haploinsufficiency for WT1 results in reduced fibroproliferation, myofibroblast accumulation, ECM production and improved lung function in both TGFα- and bleomycin-induced pulmonary fibrosis in vivo. The complexity of the molecular pathogenesis of IPF and incomplete understanding of transcriptional regulatory processes of the fibrotic machinery are obstacles to effectively treating this disease.

The development of novel anti-fibrotic therapies requires a better understanding of the molecular mechanisms that contribute to fibroblast activation and accumulation in fibrotic lung lesions. The lung development pathways and transcriptional program(s) that orchestrate fibrotic processes in IPF are poorly defined and represent a major knowledge gap in the field. Elucidation of profibrotic mechanisms has the potential to uncover novel therapeutic approaches for IPF.

Applicant has successfully generated conditional fibroblast-specific WT1 overexpression and knockout mice and demonstrated the pathogenic role of WT1 in pulmonary fibrosis. Applicant has identified anti-apoptotic genes (BCL3 and BCL2L1), MYCN, and PLK1 as important mediators of WT1-induced fibroblast activation. Loss-of-function studies suggest that MYCN functions as a positive regulator of fibroproliferation, FMT, and ECM production. It is believed that the WT1-MYCN axis may function as a positive regulator of polo-like kinase 1 (PLK1) in IPF fibroblasts. Co-immunostainings demonstrate the accumulation of MYCN and PLK1 dual positive cells in the fibrotic lesions of IPF. Further, Applicant has identified a potent inhibitor of PLK1 called Volasertib (BI 6727; Phase I/II compound), as a small molecule inhibitor that decreases WT1, MYCN and PLK1 levels in IPF fibroblasts.

MYCN is a transcription factor that is selectively expressed by epithelial cell progenitors and plays an essential role in lung development but is downregulated later in adulthood. Applicant has demonstrated dysregulated overexpression of MYCN in fibroblasts of IPF and that a TGFα model can augment fibroproliferation and ECM gene expression. A feed-forward loop of the MYCN/PLK1 axis may be involved in the excessive proliferation of cancer cells. Volasertib is a potent PLK1 inhibitor that binds and inhibits PLK1 at nanomolar doses. Applicant has demonstrated that volasertib treatment attenuates WT1, MYCN and PLK1 levels involved in fibroproliferation, survival and ECM gene expression in IPF fibroblasts WT1 is selectively upregulated in fibroblasts of the distal lung in the pathogenesis of pulmonary fibrosis. Applicant demonstrated WT1 induces MYCN in distal lung fibroblasts of IPF. Further, the upregulation of PLK1 by the WT1-MYCN axis can establish a feed-forward loop via a novel mechanism involving MYCN stabilization by PLK1. Published studies using neuroblastomas and small cell lung carcinomas support this mechanism and have shown that, indeed, PLK1 and MYCN interact to generate a feedforward loop; this loop is essential to sustain high PLK1 expression, which leads to excessive proliferation and tumor progression. However, the role of WT1 in establishing the MYCN-PLK1 axis, which augments fibroblast activation or cancer cell proliferation, has remained unexplored. Applicant observed that WT1, MYCN, and PLK1 upregulation occurs at the site of active fibrosis within IPF lungs. These areas are referred to as fibroblastic foci and subpleural fibrotic lesions. Inhibition of WT1 attenuates FMT, survival, and ECM production in IPF fibroblasts.

WT1-driven anti-apoptotic genes (BCL3, BCL2L1, etc.), MYCN, and PLK1 were previously unknown to have a role in the pathogenesis of lung scarring, in fibroproliferation, FMT, survival, and ECM production. Applicant's studies have demonstrated therapeutic efficacy of volasertib against severe fibrotic lung disease compared to FDA-approved nintedanib therapy using two alternative mouse models. A novel clinical application for volasertib in the area of pulmonary fibrosis may include volasertib therapy to prevent progression or reverse established fibrotic lung disease. Applicant's studies utilize a novel transgenic mouse model in which the pro-fibrotic growth factor TGFα is selectively and temporally overexpressed in the lung epithelium, resulting in progressive subpleural scarring, similar to the pattern seen in human IPF, and an alternative mouse model of fibrosis using repeated doses of bleomycin. Applicant's data provide compelling support that inhibiting the MYCN-PLK1 axis may be effective in arresting fibrotic lung remodeling, and may be used in patients with pulmonary fibrosis.

WT1 is a zinc-finger transcriptional regulator which has been shown to play an oncogenic role in Wilms' tumor and other hematological malignancies. WT1 is expressed at high levels in leukemic blast cells, wherein it increases the proliferation and survival of progenitor cells. However, the expression and function of WT1 have not been well studied in adult lung diseases. WT1 can be detected during lung development at mouse embryonic stages (E15.5) in the majority of mesothelial cells but not in myofibroblasts. WT1 expression in mesothelial cells is critical for embryonic lung development where WT-positive mesothelial cells transform to fibroblasts and smooth muscle cells through a novel process called mesothelial-to-mesenchymal cell transition (MMT). Homozygous WT1 mutant mice die at E13.5 to E14.5; however, heterozygous WT1 mutant mice with reduced expression of WT1 are viable, fertile, and normal in size28. During postnatal stages of lung growth, WT1 is downregulated in mesothelial cells with limited or no expression of WT1 in these cells.

Importantly, mesothelial cells do not undergo MMT during postnatal stages of lung growth or in adult lungs. However, Applicant found overexpression of WT1 in both lung fibroblasts and mesothelial cells in IPF. In support, WT1 levels were found elevated in lung fibroblasts isolated from human IPF lungs compared to normal lungs. Applicant also observed a progressive increase in the number of WT1-positive myofibroblasts in subpleural fibrotic lesions of TGFα transgenic mice with severe fibrotic lung disease, consistent with the accumulation of WT1-positive myofibroblast in IPF lungs. To determine whether mesothelial cells undergo MMT in the pathogenesis of pulmonary fibrosis, Applicant performed pulse-chase lineage tracing studies using novel WT1-reporter mice in the background of TGFαOE. These studies have demonstrated for the first time that WT1-positive mesothelial cells transform to fibroblasts and myofibroblasts and accumulate in subpleural fibrotic lung lesions. Applicant also observed that WT1 is upregulated by TGFα/EGFR signaling in fibroblasts and can cause their transformation to myofibroblasts during the progressive expansion of fibrotic lung lesions. Using preclinical models, Applicant has demonstrated that WT1 induces fibroproliferation, FMT, and ECM production in fibroblasts.

Figure 2:
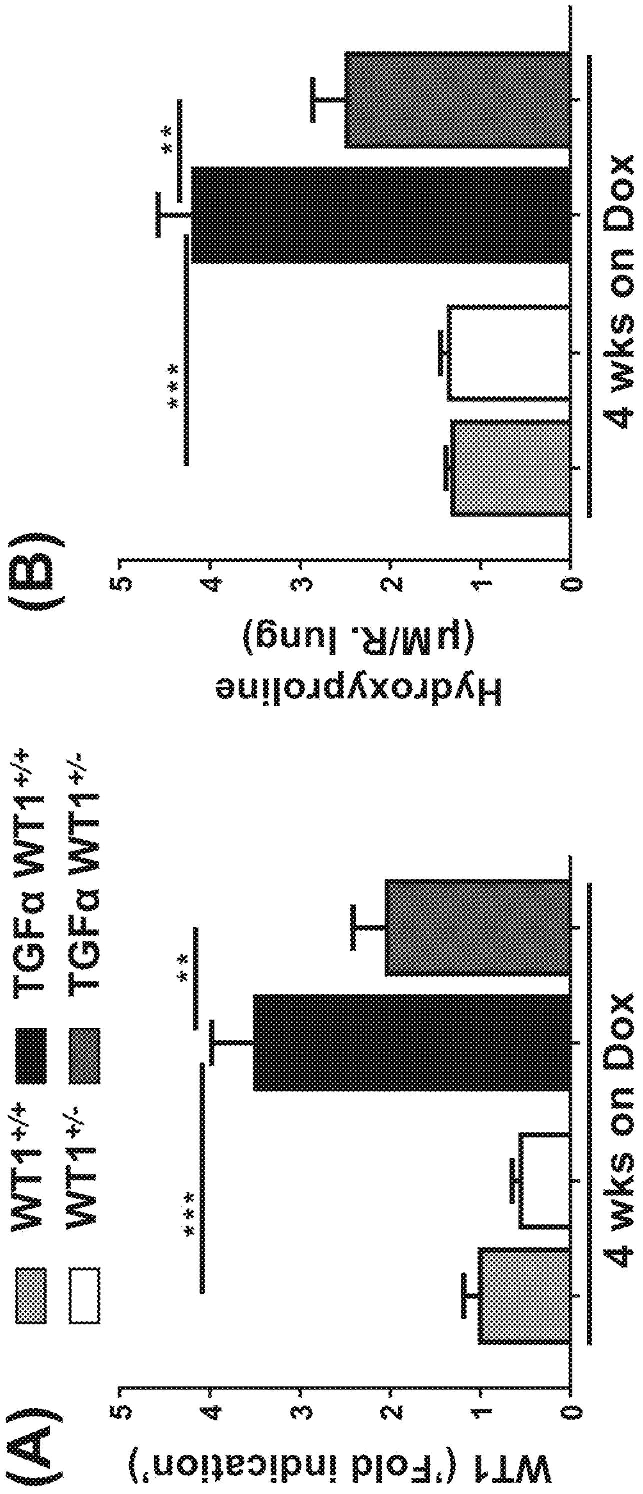
FIG. 2. The loss of WT1 attenuates pulmonary fibrosis. All four groups of mice were treated with Dox for 4 weeks. (1) WT1 transcripts quantified in the total lung using RT-PCR (B) Total right lung collagen quantified using hydroxyproline assay (N=4-5/group; *P<0.05, P<0.005, *P<0.0005.
Figure 3:
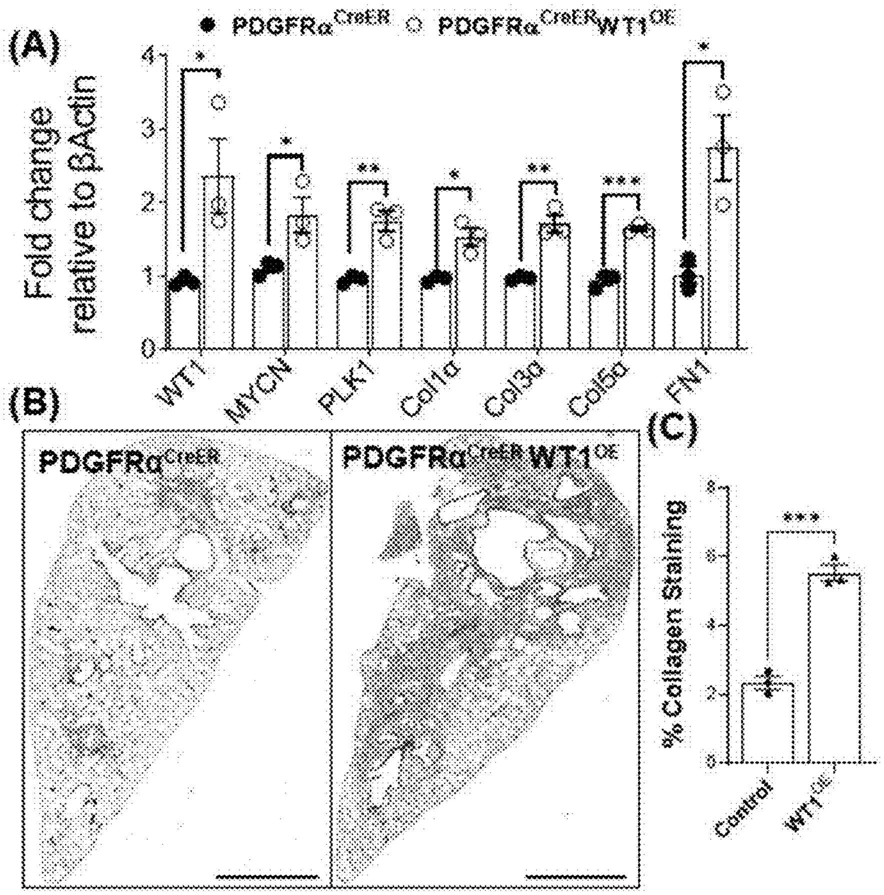
FIG. 3. Overexpression of WT1 in fibroblasts augments bleomycin-induced pulmonary fibrosis. Mice were treated with tamoxifen (twice/week) and bleomycin (day 0 and 21) for total 5 wks. (A) Transcripts of WT1, MYCN, PLK1, Col1α, Col3α, Col5α and FN1 were quantified in the total lung using RT-PCR. (B) Representative Masson's Trichrome staining for lung collagen is shown in blue. Scale bar, 1500 μm. (C) Quantification of collagen staining in lung sections of PDGFRαCreER (Control) and PDGFRαCreERWT1OE (WT1OE) mice treated with bleomycin and tamoxifen (N=3/group; *P<0.05).

Applicant found that the loss of one allele of WT1 was sufficient to attenuate both TGFα- and bleomycin-induced pulmonary fibrosis in vivo (FIG. 2). Fibroblast-specific WT1 overexpression and knockout mice have been developed. WT1 overexpression in fibroblasts led to significant increases in expression of several ECM genes, MYCN, PLK1 and collagen accumulation during bleomycin-induced pulmonary fibrosis (FIG. 3). Similarly, fibroblast-specific knockdown of WT1 was sufficient to attenuate collagen and ECM gene expression (data not shown). Applicant's findings show that WT1 is a positive regulator of several anti-apoptotic genes (BCL3, BCL2XL and BCL2L1) and the MYCN-PLK1 axis. Applicant's studies suggest that volasertib therapy effectively inhibits the feed- forward loop of the MYCN-PLK1 axis involved in fibroblast activation and pulmonary fibrosis both in vitro and in vivo. Thus, the instant disclosure relates to a previously unrecognized mechanism of fibroblast activation that focuses on therapeutic inhibition of the WT1-MYCN-PLK1 axis involved in fibroblast activation.

Figure 4:
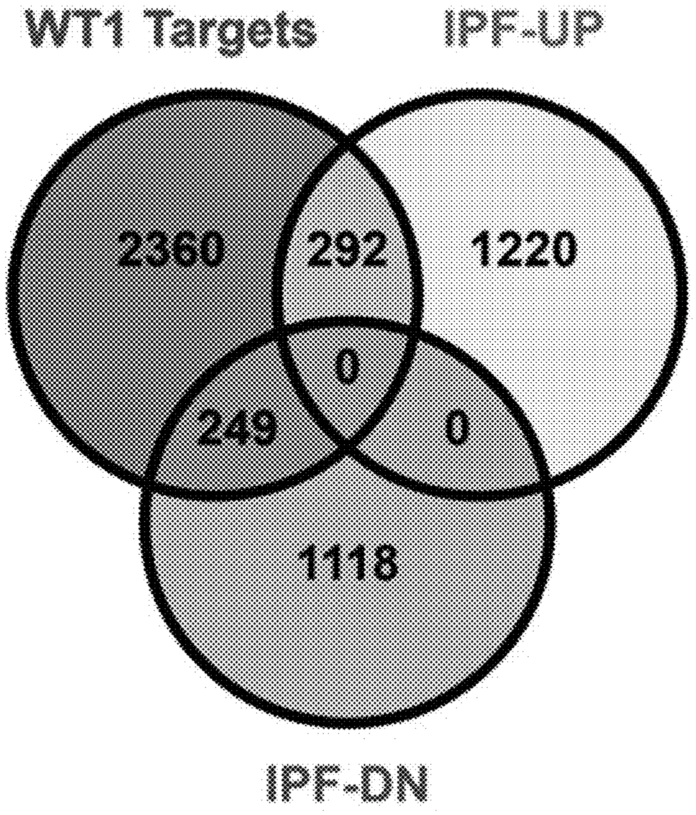
FIG. 4. Comparative analysis of WT1 target genes identified using ChIP-seq that either up- or down-regulated in IPF lungs.
Figure 5:
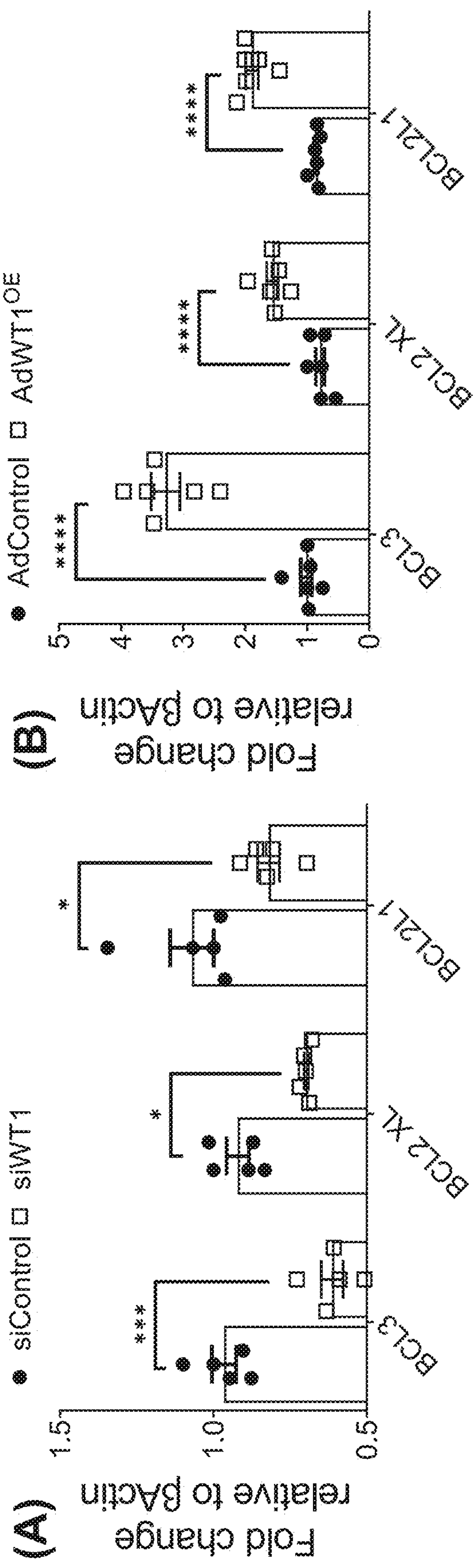
FIG. 5. WT1 is positive regulator of anti-apoptotic gene expression. (A) The loss of WT1 attenuated anti-apoptotic gene transcript levels including BCL3, BCL2XL, and BCL2L2 in IPF fibroblasts. (B) Overexpression of WT1 induces pro-apoptotic gene transcript levels including BCL3, BCL2XL, and BCL2L2 in normal fibroblasts. *P<0.05.
Figure 6:
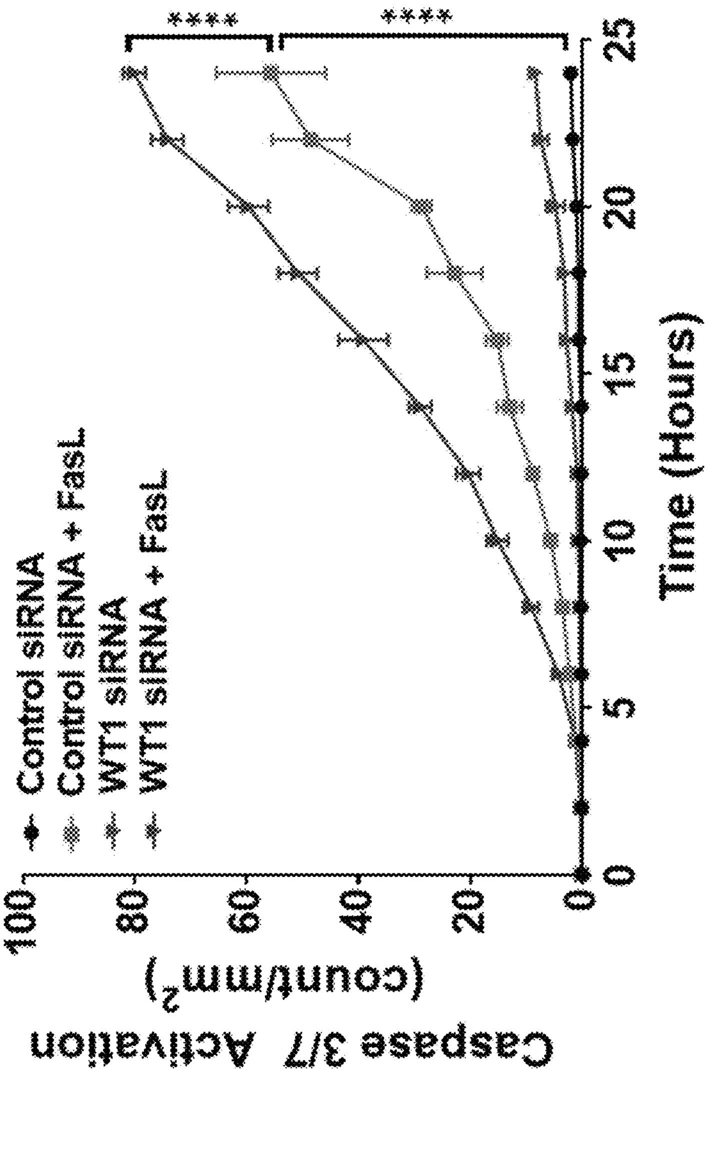
FIG. 6. WT1 is a positive regulator of fibroblast survival. IPF fibroblasts were treated with control or WT1-specific siRNA for 48 hours, and FasL-induced apoptosis was analyzed. ****P<0.00005.

Mechanisms underlying fibroblast activation by transcriptional regulators including WT1 have been investigated. Applicant explored the possible regulation of IPF-specific gene transcripts by WT1 with the help of WT1 ChIP-seq analysis and found evidence for more than 500 WT1 target genes (with putative human-mouse conserved WT1 binding sites within the promoter region) are differentially expressed in IPF lungs (FIG. 4). To generate WT1-driven gene networks in pulmonary fibrosis, Applicant inhibited endogenous WT1 expression using siRNA in lung fibroblasts isolated from fibrotic lungs and performed total RNA seq analysis. Reduced WT1 levels resulted in down-regulation of approximately 1425 transcripts that are involved in the activation of lung fibroblasts and identified fibroproliferation, mesenchymal growth, and ECM production as the major mesenchymal cell-specific biological processes activated by WT1 in IPF. The persistence of myofibroblasts in injured lung tissue is a major cause of non-resolving fibrosis. The successful resolution of fibrosis is not only dependent on inhibiting myofibroblast differentiation, but also requires eliminating apoptosis-resistant myofibroblasts. Applicant identified several anti-apoptotic gene transcripts that were upregulated in fibroblasts of both IPF and TGFα model. To identify the role of WT1 in myofibroblast apoptosis, Applicant treated IPF fibroblasts isolated from fibrotic lesions of IPF lungs with control or WT1-specific siRNA for 72 hours. The knockdown of WT1 resulted in reduced expression of several anti-apoptotic gene transcripts in IPF fibroblasts (FIG. 5, A). Similarly, overexpression of WT1 was sufficient to augment anti-apoptotic gene expression in normal fibroblasts (FIG. 5, B). Live images of cells undergoing caspase-3/7 mediated apoptosis were acquired. Applicant found that the loss of WT1 was sufficient to induce apoptosis in IPF fibroblasts (FIG. 6). Applicant also assessed whether FAS-induced apoptosis is WT1 dependent. In support of Applicant's hypothesis, a significant increase in FAS-induced apoptosis with the loss of WT1 in IPF fibroblasts was observed.

Figure 7:
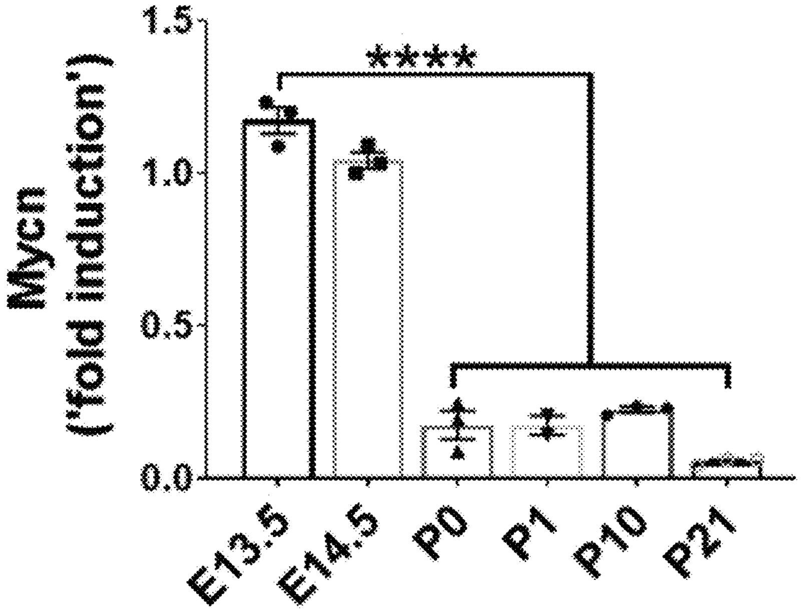
FIG. 7. MYCN expression during lung development. MYCN transcripts decrease in the postnatal period of lung development. ****p<0.00005.
Figure 8:
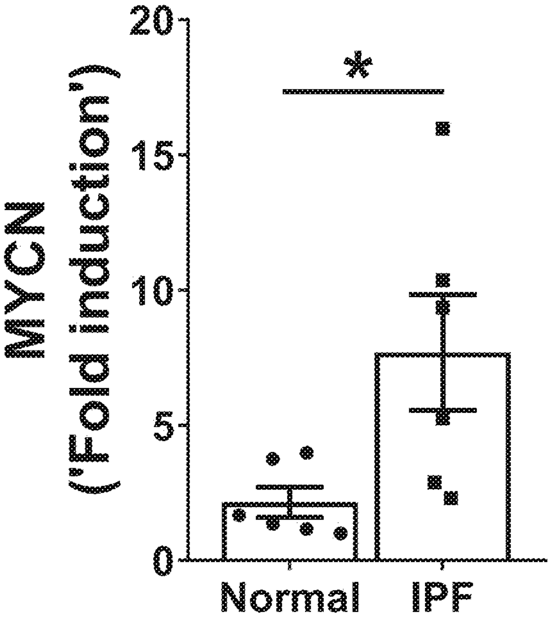
FIG. 8. Upregulation of MYCN in IPF Lungs. MYCN transcript levels are increased in total transcripts of IPF lungs compared to normal lungs. *p<0.05.
Figure 9:
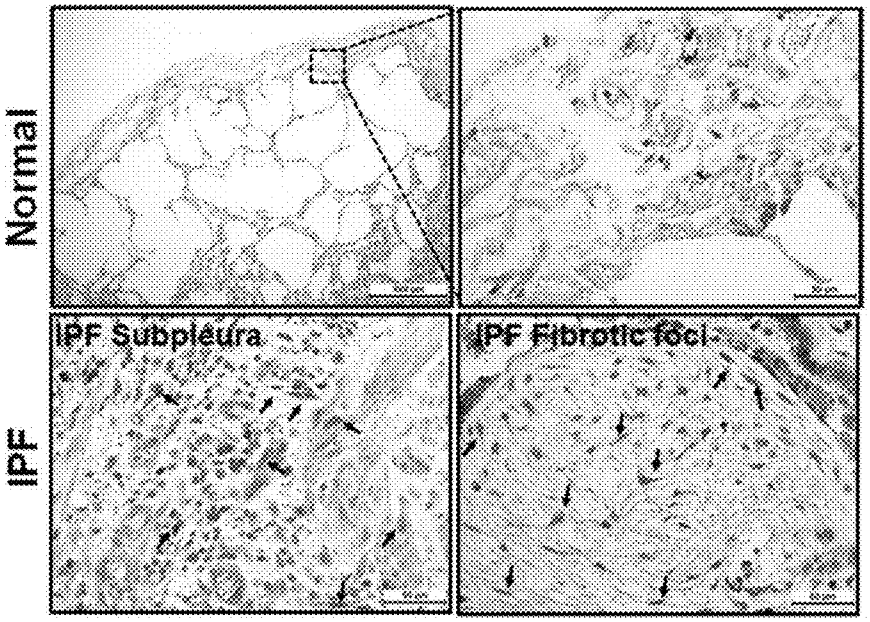
FIG. 9. MYCN-positive fibroblasts accumulate in the distal areas of IPF Lungs. Top Panels: Normal lung shown at low (Scale bar, 500 μm) and high magnification (Scale bar, 50 ρm). Bottom Panels: Spindle-shaped nuclei of MYCN-positive fibroblasts indicated using arrows in high magnification images of subpleura and fibrotic foci of IPF lung. Scale Bar, 50 μm.
Figure 10:
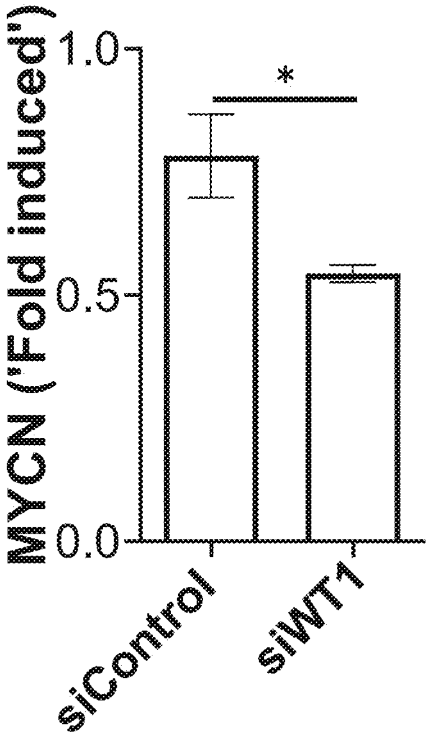
FIG. 10. WT1 is a positive regulator of MYCN expression. The knockdown of WT1 attenuates MYCN expression in lung resident fibroblasts isolated from IPF lungs (N=3; *p<0.05).
Figure 11:
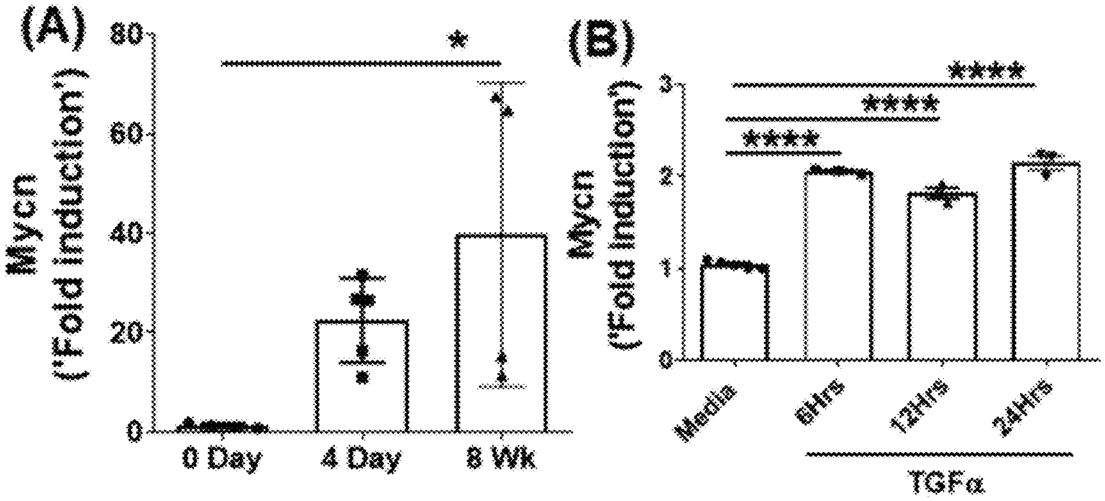
FIG. 11. TGFα induces MYCN expression in fibroblasts. (A) MYCN transcripts were increased in the lungs of TGFα mice on Dox for 4 days and 8 wks compared to 0 day controls. (B) Human lung fibroblasts were treated with TGFα for 6, 12 and 24 hrs and MYCN transcripts were quantified using RT-PCR. *p<0.05.
Figure 12:
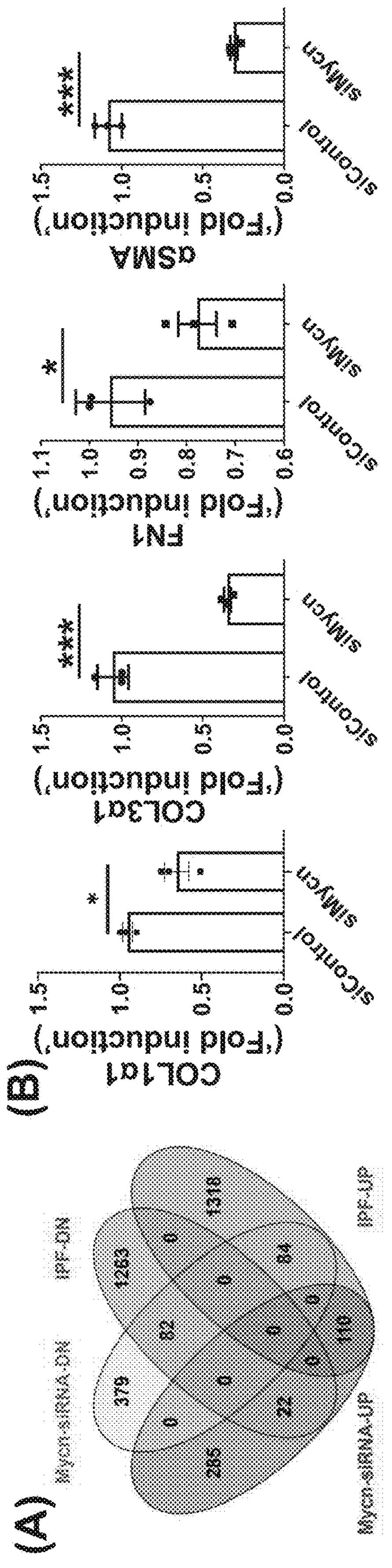
FIG. 12. MYCN induces ECM gene expression in fibroblasts. (A)Venn diagram depicting the overlap of differentially expressed genes in IPF lungs that are significantly reversed upon MYCN knockdown in fibroblasts isolated from the fibrotic lesions of TGFα mice on Dox for 4 wks. (B) IPF fibroblasts were treated with control or MYCN-specific siRNA for 72 hrs and measured ECM genes using RT-PCR. *p<0.05.

WT1 is a positive regulator of the MYCN. MYCN is a member of the MYC family of transcription factors that contain a basic helix-loop-helix (bHLH) domain. MYCN is selectively expressed by distal epithelial cells (type II cells and bronchial epithelium) but not mesenchyme to support the outgrowth of lung buds and branching of the respiratory tree during lung development. In support, the selective deletion of MYCN in the epithelium of the developing lung had led to the reduced proliferation in the distal epithelium, and highly enlarged air spaces. In contrast, overexpression of MYCN selectively in the distal epithelial cells has resulted in abnormal lung growth marked by impaired differentiation of type II cells and formation of aberrant mesenchyme in the distal regions of developing lungs. Thus MYCN is essential in the developing lung for maintaining a distal population of epithelial progenitor cells. However, MYCN expression is downregulated in the distal lung epithelium of adult lungs compared to embryonic stages of lung development (FIG. 7). Transcription factors of lung development may be reactivated in multiple lung cells in the pathogenesis of IPF. Applicant's studies demonstrate WT1 upregulation in fibroblasts of IPF and mouse models. Applicant assessed whether MYCN is upregulated in IPF and found a significant increase in MYCN levels in IPF lungs compared to control lungs (FIG. 8) Immunostainings suggest MYCN is expressed by spindle-shaped cells that accumulate in fibrotic lesions of IPF compared to limited or no expression in normal lungs (FIG. 9). To determine the role of WT1 in MYCN expression, Applicant isolated IPF fibroblasts and treated them with WT1-specific siRNA or control siRNA for 72 hrs. A significant decrease in MYCN transcripts in IPF fibroblasts treated with WT1-specific siRNA compared to control siRNA was observed (FIG. 10). Activation of EGFR signaling by TGFα has been shown to augment fibroblast activation including fibroproliferation, differentiation, migration, and survival. An increase in TGFα levels in IPF was demonstrated in IPF.

Figure 13:
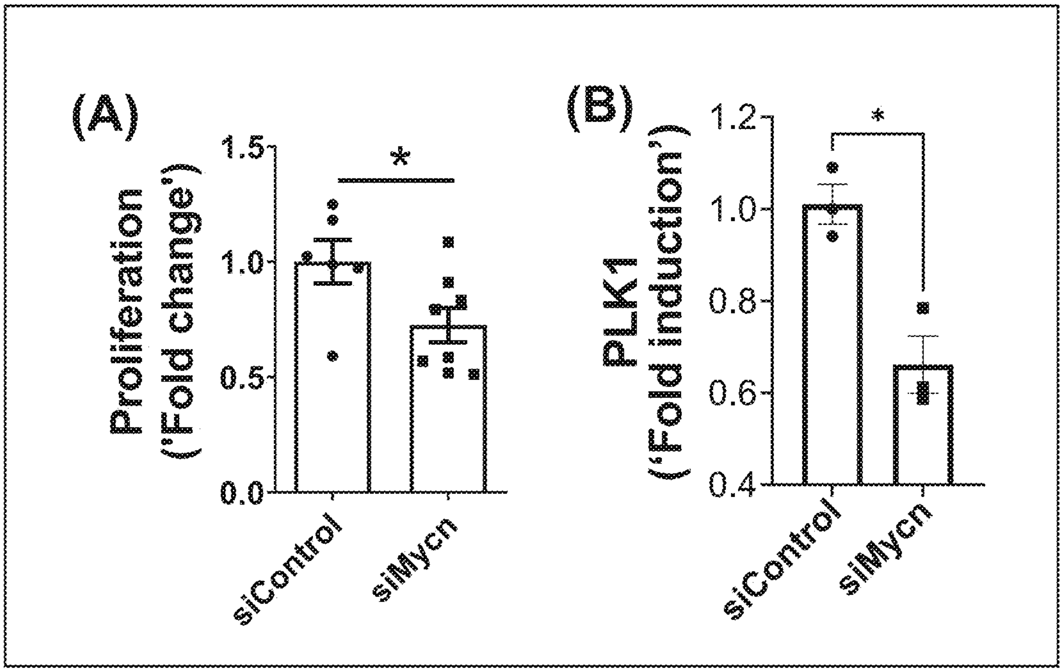
FIG. 13. MYCN is a positive regulator of PLK1 and fibroproliferation. (A) The knockdown of MYCN attenuates fibroproliferation as measured by Brdu incorporation into IPF fibroblasts. (B) The loss of MYCN attenuates PLK1 gene expression in IPF fibroblasts. *p<0.05.
Figure 14:
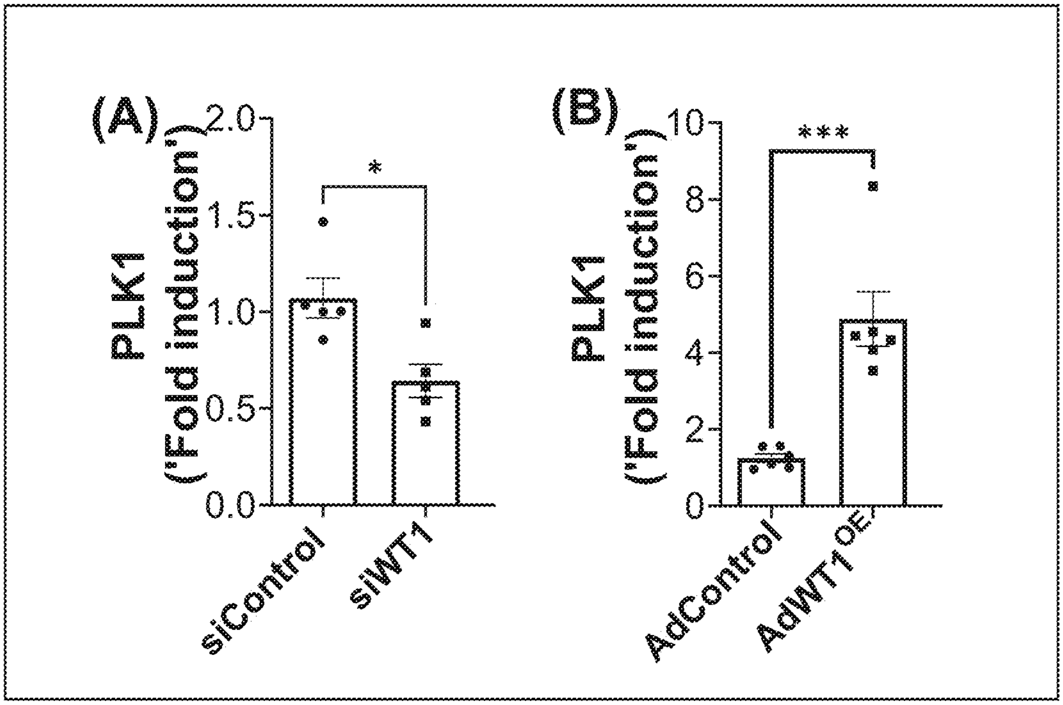
FIG. 14. WT1 is a positive regulator of PLK1. (A) The loss of WT1 attenuated PLK1 in IPF fibroblasts. (B) The overexpression of WT1 induces PLK1 expression in normal fibroblasts. $*p<0.05$.
Figure 15:
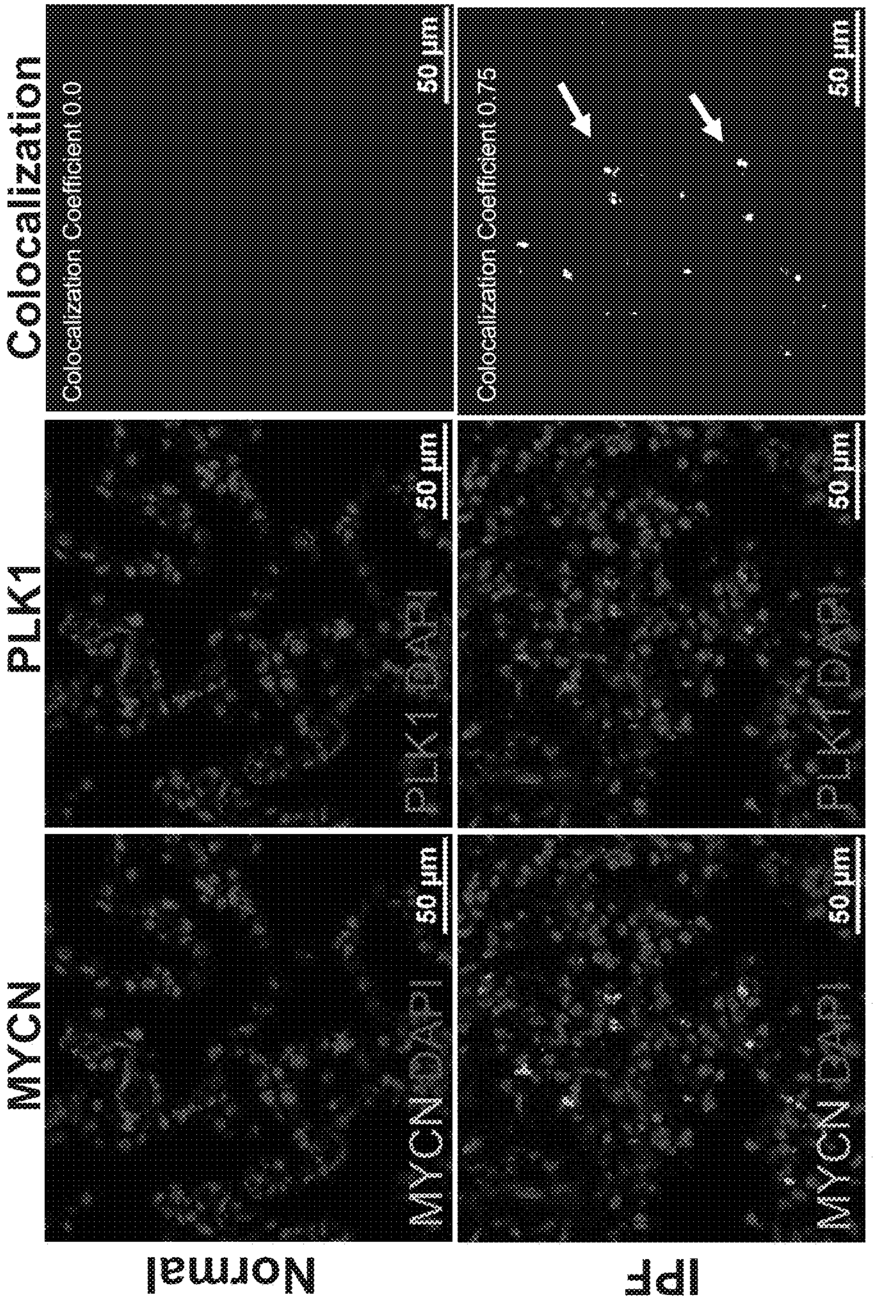
FIG. 15. MYCN and PLK1 dual positive cells accumulate in the fibrotic lesions of IPF. Normal and IPF lung sections were co-immunostained with antibodies against MYCN (green) and PLK1 (red). Colocalization image shows MYCN colocalized with PLK1 (white). Scale bar 50 micrometers.

To further determine mechanisms of TGFα-driven lung fibrosis, transgenic mice were generated that conditionally overexpressed TGFα in the lung epithelium after receiving doxycycline (Dox), using the CCSP rtTA promoter. Overexpression of TGFα was sufficient to cause severe fibrosis and lung function decline. To further investigate the role of the TGFα-WT1 axis in MYCN upregulation, Applicant quantified MYCN transcripts in the lungs of TGFαOE mice and observed a significant a possible reciprocal activation between PLK1 and MYCN is involved in tumorigenesis. Therefore, PLK1 expression was measured in IPF fibroblasts treated with MYCN-specific or control siRNA. The loss of MYCN was sufficient to attenuate PLK1 levels in IPF fibroblasts (FIG. 13B). To determine the role of WT1 in PLK1 expression, Applicant performed the knockdown or overexpression of WT1; the findings suggest that WT1 functions as a positive regulator of PLK1 in fibroblasts (FIG. 14). To determine whether MYCN and PLK1 are co-expressed in cells that accumulate in fibrotic lesions of IPF, Applicant performed co-immunostainings and assessed colocalization between MYCN and PLK1. As shown in FIG. 15, both MYCN and PLK1 were observed to be upregulated and co-localized in fibrotic lesions of IPF compared to control lungs. Taken together, these findings strongly support that the WT1-MYCN-PLK1 axis functions as a positive regulator of fibroblast activation in IPF.

Figure 16:
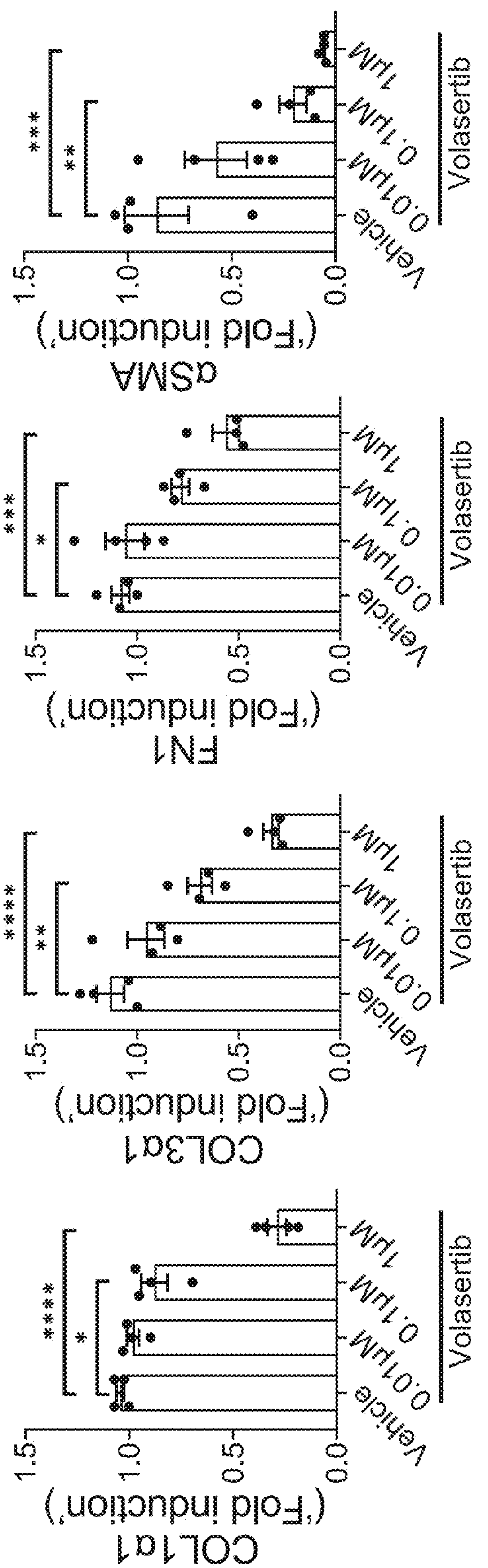
FIG. 16. Inhibition of PLK1 using volasertib attenuates ECM gene expression. IPF fibroblasts were treated with vehicle or volasertib for 16 hours and ECM-associated gene transcripts Col1α, Col3α1, FN1, and αSMA) were measured using RT-PCR. $*p<0.05$.
Figure 17:
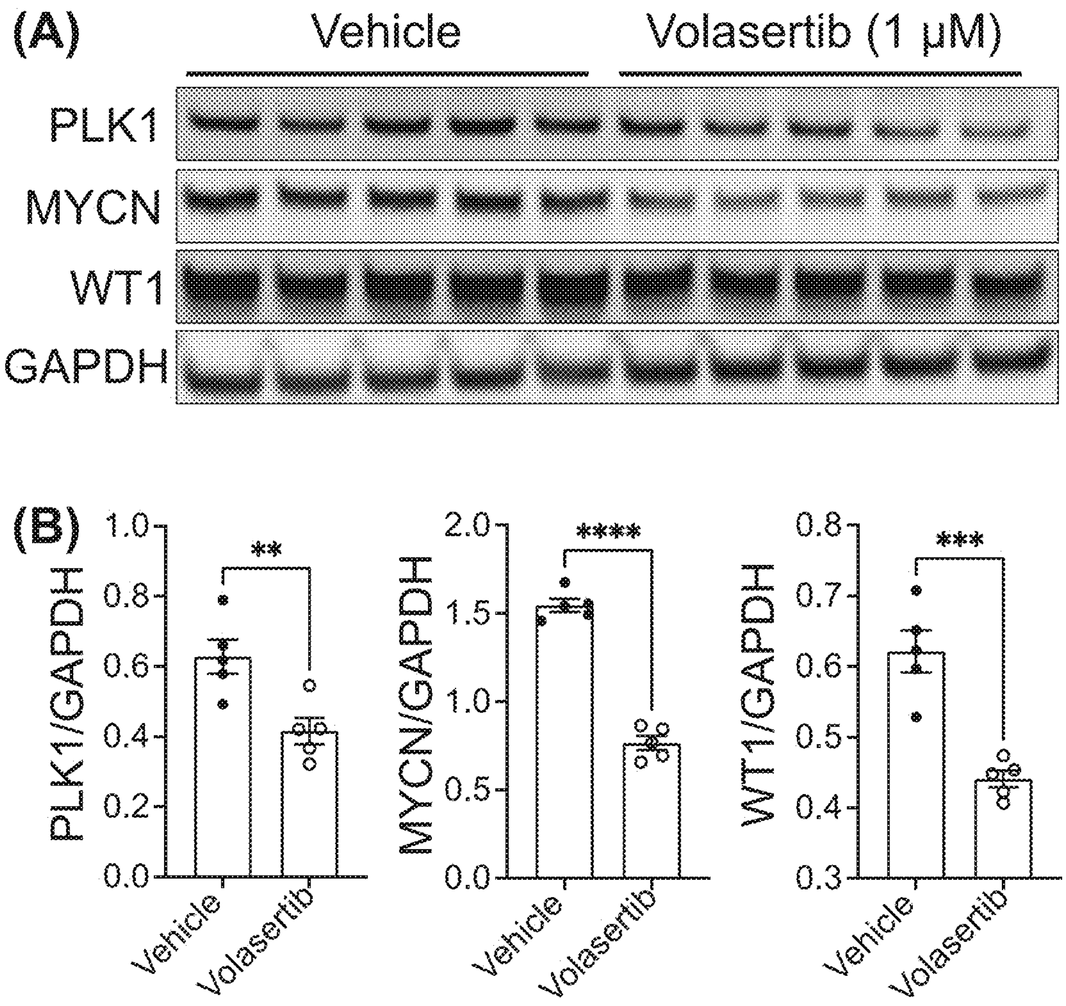
FIG. 17. Volasertib treatment attenuates the WT1-MYCN-PLK1 axis in IPF fibroblasts. IPF fibroblasts were treated with vehicle or volasertib (1 μM) for 48 hours and measured PLK1, MYCN and WT1 protein levels in cell lysates using western blots and normalized to GAPDH. $*P<0.05$.
Figure 18:
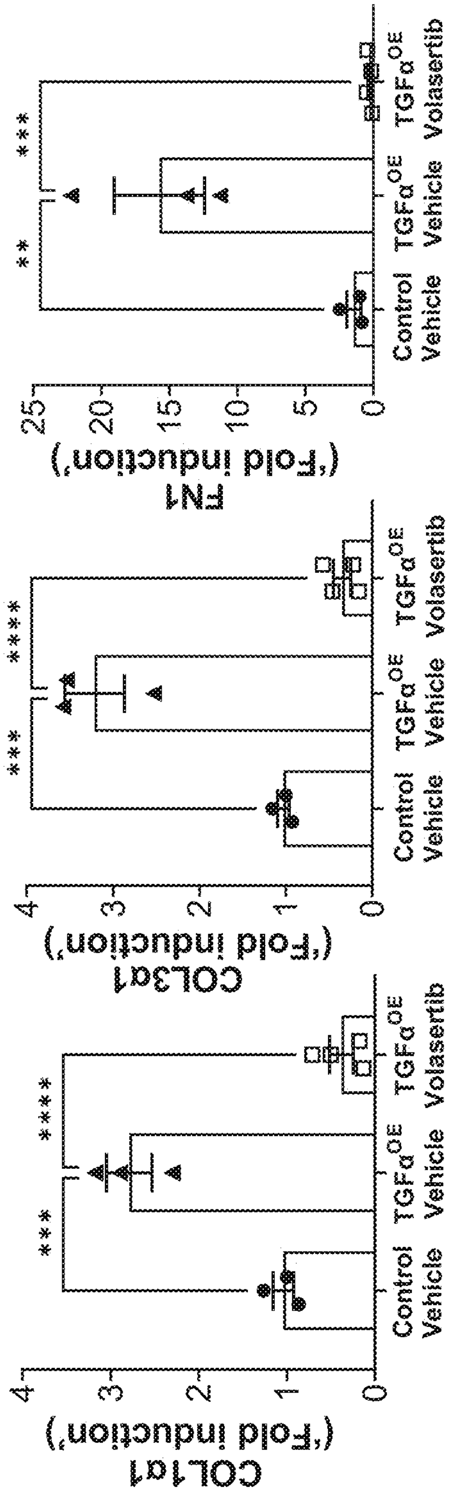
FIG. 18. In vivo inhibition of PLK1 with volasertib attenuates ECM gene expression during TGFα-induced pulmonary fibrosis.
Figure 19:
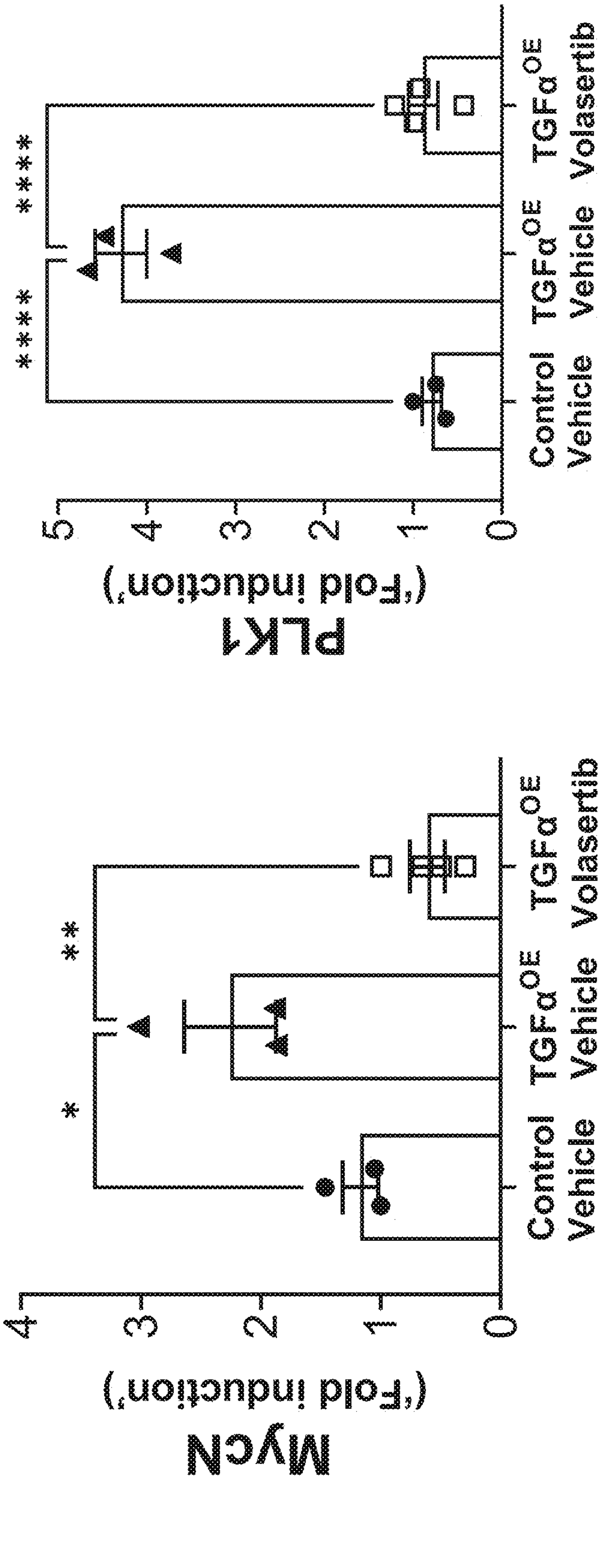
FIG. 19. In vivo inhibition of PLK1 with volasertib attenuates MYCN and PLK1 during TGFα induced pulmonary fibrosis.

Pharmacological inhibition of PLK1 attenuates the WT1-MYCN-PLK1 axis. In vitro knockdown studies demonstrate that the MYCN-PLK1 axis increases fibroproliferation and ECM production. In support, the treatment of IPF fibroblasts with volasertib was sufficient to attenuate ECM gene expression (FIG. 16). Volasertib treatment was sufficient to attenuate MYCN, WT1 and PLK1 levels in IPF fibroblasts (FIG. 17). To determine in vivo therapeutic effects of volasertib, TGFα mice were treated simultaneously with volasertib (30 mg/kg; QD) and Dox for five days, a period that leads to activation of WT1, MYCN and PLK1 in fibroblasts. Volasertib treatment has attenuated ECM gene expression including Col1α1, Col3a1, and FN1 in mice treated with volasertib compared vehicle-treated fibrosis controls (FIG. 18). Notably, volasertib therapy was able to attenuate both MYCN and PLK1 levels in lungs during TGFα-induced pulmonary fibrosis (FIG. 19). Also, H&E stainings suggest no toxicity with volasertib therapy at the doses tested (data not shown). Together, in vivo studies have established that inhibiting PLK1 is sufficient to attenuate the WT1-MYCN-PLK1 axis involved in fibroblast activation and pulmonary fibrosis.

Figure 20:
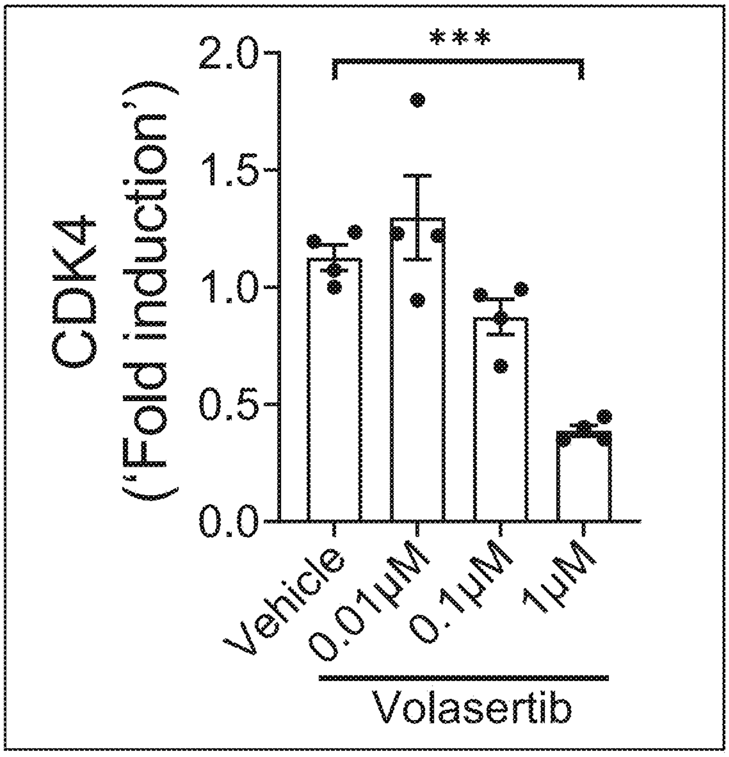
FIG. 20. Inhibition of PLK1 using volasertib attenuates CDK4 gene expression. IPF fibroblasts were treated with vehicle or volasertib for 16 hours and CDK1 involved in fibroproliferation was measured using RT-PCR. $*P<0.05$.
Figure 21:
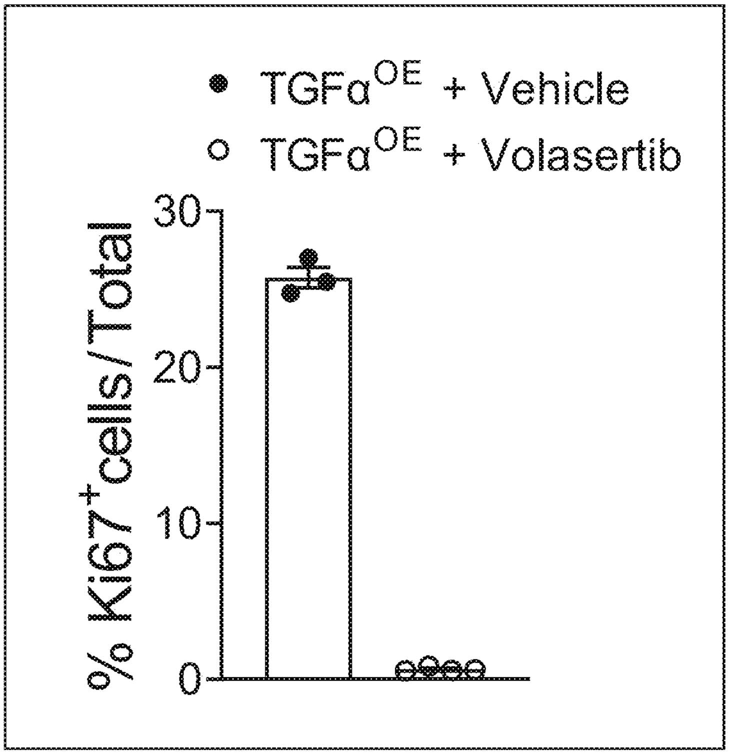
FIG. 21. In vivo inhibition with volasertib attenuates ECM gene expression during TGFα-induced pulmonary fibrosis. $*P<0.05$.

In vitro apoptotic assays demonstrate that WT1 is a positive regulator of anti-apoptotic gene expression and fibroblast survival in IPF (FIG. 5 & FIG. 6). Since WT1 is required for the expression of pro-apoptotic gene expression, it is plausible that their loss influences myofibroblast survival in IPF. Further, promoter analysis of WT1 target genes has identified BCL3 and BCL2L1 as potential target genes with WT1 binding elements (FIG. 20).

All percentages and ratios are calculated by weight unless otherwise indicated.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. All accessioned information (e.g., as identified by PUBMED, PUBCHEM, NCBI, UNIPROT, or EBI accession numbers) and publications in their entireties are incorporated into this disclosure by reference in order to more fully describe the state of the art as known to those skilled therein as of the date of this disclosure. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications may be made without departing from the spirit and scope of the invention. It is therefore intended to cover in the appended claims all such changes and modifications that are within the scope of this invention.

What is claimed is:

1. A method for treating an individual for idiopathic pulmonary fibrosis comprising administering volasertib, or a salt thereof, or hydrate thereof.

2. The method of claim 1 wherein said administering is in an amount and for a duration of time effective to attenuate fibrosis progression associated with pulmonary fibrosis.

3. The method of claim 1 wherein said administering is in an amount and for a duration of time effective to achieve one or more outcomes selected from decreased invasiveness of pulmonary fibroblasts, increased clearance of myofibroblasts, decreased migration of pulmonary fibroblasts, decreased pulmonary fibroblast proliferation, decreased cell adhesion of pulmonary fibroblasts, decreased myofibroblast activation, decreased extracellular matrix (ECM) accumulation or production, and improved lung function.

4. The method of claim 1 wherein said administering is in an amount and for a duration of time effective to improve lung function, wherein lung function is measured by one or more of spirometry, pulse oximetry, exercise stress test or arterial blood gas test.

5. The method of claim 1, further comprising administering a second agent selected from one or more of nintedanib, pirfenidone, tocilizumab, nivolumab, pembrolizumab, pidilizumab, lambrolizumab, atezolizumab, durvalumab, avelumab, ofnivolumab, and ipilmumab.

6. The method of claim 5, wherein said second agent is administered prior to said volasertib administration.

7. The method of claim 1, wherein said administration comprises a loading dose and a maintenance dose.

8. The method of claim 1, wherein said administration comprises a loading dose and a maintenance dose, wherein said loading dose is larger than said maintenance dose.

9. The method of claim 1, wherein said individual is an adult.

10. The method of claim 1, wherein said individual is under 18 years of age.

11. The method of claim 1, wherein said individual is pre-pubescent.

12. The method of claim 1, wherein said administration is selected from one or more of oral, parenteral, intravenous, and subcutaneous.

13. The method of claim 1, wherein said administration is via inhalation.

14. The method of claim 1, wherein said volasertib is administered at an interval selected from twice a day, three times a day, daily, every other day, every three days, every four days, every five days, every six days, weekly, every two weeks, every three weeks, and monthly.

15. The method of claim 5, wherein said second agent is administered simultaneously with said volasertib administration.

16. The method of claim 5, wherein said second agent is administered after said volasertib administration.

17. The method of claim 1, wherein the administering comprises administering to the individual from 90 mg to 500 mg of volasertib, or a salt thereof, or hydrate thereof.

* * * * *